(12) United States Patent
Tokhtuev et al.

(10) Patent No.: US 7,550,746 B2
(45) Date of Patent: Jun. 23, 2009

(54) UV FLUOROMETRIC SENSOR AND METHOD FOR USING THE SAME

(75) Inventors: Eugene Tokhtuev, Duluth, MN (US); Christopher J. Owen, Duluth, MN (US); Viktor Slobodyan, Duluth, MN (US); Anatoly Skirda, Duluth, MN (US); Paul Schilling, Duluth, MN (US); Anna Pilipchenko, Duluth, MN (US); Paul R. Kraus, Apple Valley, MN (US); Katherine M. Sanville, White Bear Lake, MN (US); Joseph Phillip Erickson, Cloquet, MN (US)

(73) Assignee: Ecolab Inc., Saint Paul, MN (US)

( * ) Notice: Subject to any disclaimer, the term of this patent is extended or adjusted under 35 U.S.C. 154(b) by 0 days.

(21) Appl. No.: 11/809,208

(22) Filed: May 31, 2007

(65) Prior Publication Data
US 2008/0030712 A1 Feb. 7, 2008

Related U.S. Application Data

(60) Provisional application No. 60/809,844, filed on Jun. 1, 2006.

(51) Int. Cl.
G01N 21/64 (2006.01)
G01J 3/00 (2006.01)
(52) U.S. Cl. ..................... 250/461.1; 356/51
(58) Field of Classification Search .......... 250/253, 250/301, 573, 459.1, 461.1
See application file for complete search history.

(56) References Cited

U.S. PATENT DOCUMENTS 4,084,905 A 4/1978 Schreiber et al.
4,394,573 A 7/1983 Correa et al.

(Continued)

FOREIGN PATENT DOCUMENTS

JP 2001228139 8/2001

(Continued)

OTHER PUBLICATIONS

Notification of the Transmittal of the International Search Report and Written Opinion, from corresponding PCT Application Serial No. PCT/US2007/012860, mailed Nov. 8, 2007, 13 pages.

(Continued)

Primary Examiner—David P Porta
Assistant Examiner—Faye Boosalis
(74) Attorney, Agent, or Firm—Shumaker & Sieffert, P.A.

(57) ABSTRACT

An ultraviolet (UV) fluorometric sensor measures a chemical concentration in a sample based on the measured fluorescence of the sample. The sensor includes a controller, at least one UV light source, and at least one UV detector. The sensor emits UV light in a wavelength range of 245-265 nm from the light source through the sample in an analytical area. The UV detector measures the fluorescence emission from the sample. The controller transforms output signals from the UV detector into fluorescence values or optical densities for one or more wavelengths in the wavelength range of 265-340 nm. The controller calculates the chemical concentration of the chemical in the sample based on the measured fluorescence emissions.

20 Claims, 24 Drawing Sheets

U.S. PATENT DOCUMENTS

| | | | |
|---|---|---|---|
| 4,767,206 A | | 8/1988 | Schwartz |
| 4,791,056 A | | 12/1988 | Sizto et al. |
| 4,804,849 A | | 2/1989 | Booth et al. |
| 5,059,790 A | | 10/1991 | Klainer et al. |
| 5,242,869 A | | 9/1993 | Tarumi et al. |
| 5,304,492 A | * | 4/1994 | Klinkhammer .............. 436/52 |
| 5,689,110 A | | 11/1997 | Dietz et al. |
| 5,932,860 A | | 8/1999 | Plesko |
| 6,348,965 B1 | | 2/2002 | Palladino et al. |
| 6,608,675 B1 | | 8/2003 | Ishikawa |
| 6,977,729 B2 | | 12/2005 | Marquardt et al. |
| 7,198,755 B2 | | 4/2007 | Tokhtuev et al. |
| 2002/0036276 A1 | * | 3/2002 | Seeman ..................... 250/573 |
| 2002/0126289 A1 | | 9/2002 | Marquardt et al. |

FOREIGN PATENT DOCUMENTS

| | | |
|---|---|---|
| WO | WO/93/16225 A1 | 8/1993 |
| WO | WO/94/07127 A1 | 3/1994 |
| WO | WO/2005/119216 A1 | 12/2005 |

OTHER PUBLICATIONS

U.S. Appl. No. 11/299,784, filed Dec. 13, 2005, entitled, "Calibrator for a Fluorosensor (Amended)", Tokhtuev et al.

* cited by examiner

UV FLUOROMETRIC SENSOR AND METHOD FOR USING THE SAME

CROSS-REFERENCE TO RELATED APPLICATION

This application claims the benefit of U.S. provisional Application Ser. No. 60/809,844, filed Jun. 1, 2006, the entire content of which is incorporated herein by reference.

FIELD OF THE INVENTION

The invention generally relates to a fluorometric sensor for testing a liquid or gaseous sample, and more particularly to a UV fluorometric sensor for determining and monitoring chemical concentration(s) in a sample.

BACKGROUND

Absorption spectroscopy is concerned with the range of electromagnetic spectra absorbed by a substance. In application Ser. No. 11/311,126, filed on Dec. 20, 2005, UV/VIS spectroscopy is used to obtain absorption information of a sample placed in a spectrophotometer. Ultraviolet and/or visible light at a certain wavelength (or range of wavelengths) is shined through the sample. The spectrophotometer measures how much of the light is absorbed by the sample.

Fluorometric spectroscopy concerns detection of fluorescent spectra emitted by a sample of interest. It involves using a beam of light, usually ultraviolet (UV) light, that excites the electrons in molecules of certain compounds in the sample and causes them to emit light of a lower energy. This lower energy light is typically, but not necessarily, visible light. This technique is popular in biochemical and medical applications, such as confocal microscopy, fluorescence resonance energy transfer and fluorescence lifetime imaging. Molecular fluorescence spectroscopy instrumentation generally consists of a source of excitation radiant energy, an excitation wavelength selector, a sample cell to contain the analyte material, an emission wavelength selector, a detector with signal processor and a readout device.

There are several types of fluorometers for measuring fluorescence. Filter fluorometers use optical filters to isolate the incident light and fluorescent light. Spectrofluorometers use diffraction grating monochromators to isolate the incident light and fluorescent light. In these devices, the spectrum consists of the intensity of emitted light as a function of the wavelength of either the incident light (excitation spectrum) or the emitted light, or both.

In cleaning and antimicrobial operations, commercial users, such as restaurants, hotels, food and beverage plants, grocery stores and the like, rely upon the concentration of the cleaning or antimicrobial product to make the product work effectively. Failure of a cleaning or antimicrobial product to work effectively (due to concentration issues) can cause a customer or consumer to perceive the cleaning and antimicrobial product as lower quality and the commercial users being perceived as organizations providing inferior services. In addition, they may be investigated and/or sanctioned by government regulatory and health agencies. Accordingly, there is a need for a system that can determine if the concentration of a product is within a specified concentration range. The same may be true for other applications, such as water care, pest control, beverage and bottling operations, packaging operations, and the like.

SUMMARY

Surprisingly, it has been discovered that the concentration of a product in a sample containing a chemical that exhibits fluorescence characteristics can be determined using a fluorometric sensor that measures the fluorescence of the sample and calculates the concentration of the chemical based on the measured fluorescence.

In one embodiment, the invention is directed to a sensor comprising an ultraviolet (UV) light source that emits a first UV wavelength through a sample containing a chemical that exhibits fluorescent characteristics, a UV detector that detects fluorescence emissions of the sample at a second UV wavelength and a controller that calculates the concentration of the chemical in the sample based on the detected fluorescence emission.

In another embodiment, the invention is directed to a method comprising emitting an ultraviolet (UV) light having a first UV wavelength through an analytical area of a sample, wherein the sample contains a chemical that exhibits fluorescent characteristics in the analytical area, measuring a fluorescence emission of the sample at a second UV wavelength and calculating the concentration of the chemical in the sample based on the measured fluorescence emission.

The method may also include measuring a fluorescence emission of a zero solution having zero concentration of the chemical and calculating the concentration of the chemical in the sample based on the calculated difference in the measured fluorescence emission of the sample and the measured fluorescence emission of the zero solution. The method may also include determining a calibration constant found for known concentrations of the chemical.

The details of one or more embodiments of the invention are set forth in the accompanying drawings and the description below. Other features of the invention will be apparent from the description and drawings, and from the claims.

DETAILED DESCRIPTION

The UV fluorometric sensor of the present invention determines the concentration of a chemical in a sample. The sensor measures the UV fluorescence emission of a sample containing a chemical which has fluorescent characteristics. The concentration of the product is then calculated based on the fluorescence measurement(s). There are many different compounds that have fluorescent characteristics to be used in different applications as discussed later.

To measure/monitor chemical concentrations in a sample automatically, continuously, and with a high sensitivity, the invention uses a fluorometric sensor to measure fluorescence properties of the chemical(s) in the sample and calculate the chemical concentration(s) in the sample based on the measured fluorescence values. Surprisingly, it has been discovered that the sensor of the present invention is especially effective over the near UV (200-380 nm wavelength).

Figure 1A:
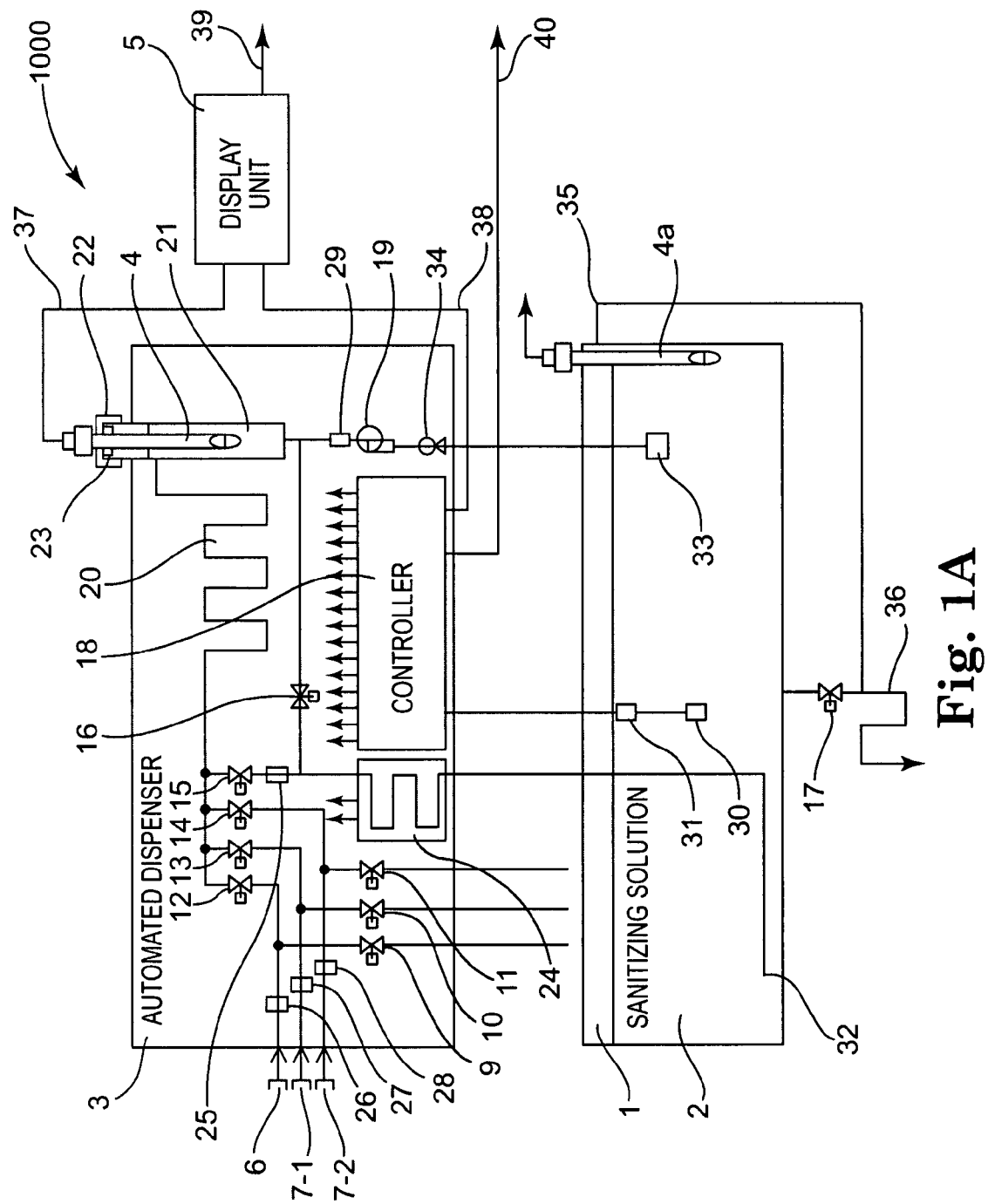
FIG. 1A shows a block diagram of a fluorometric sensing system 1000 for measuring chemical concentration in a liquid or gaseous sample (e.g. a sanitizer) according to the invention.
Figure 1B:
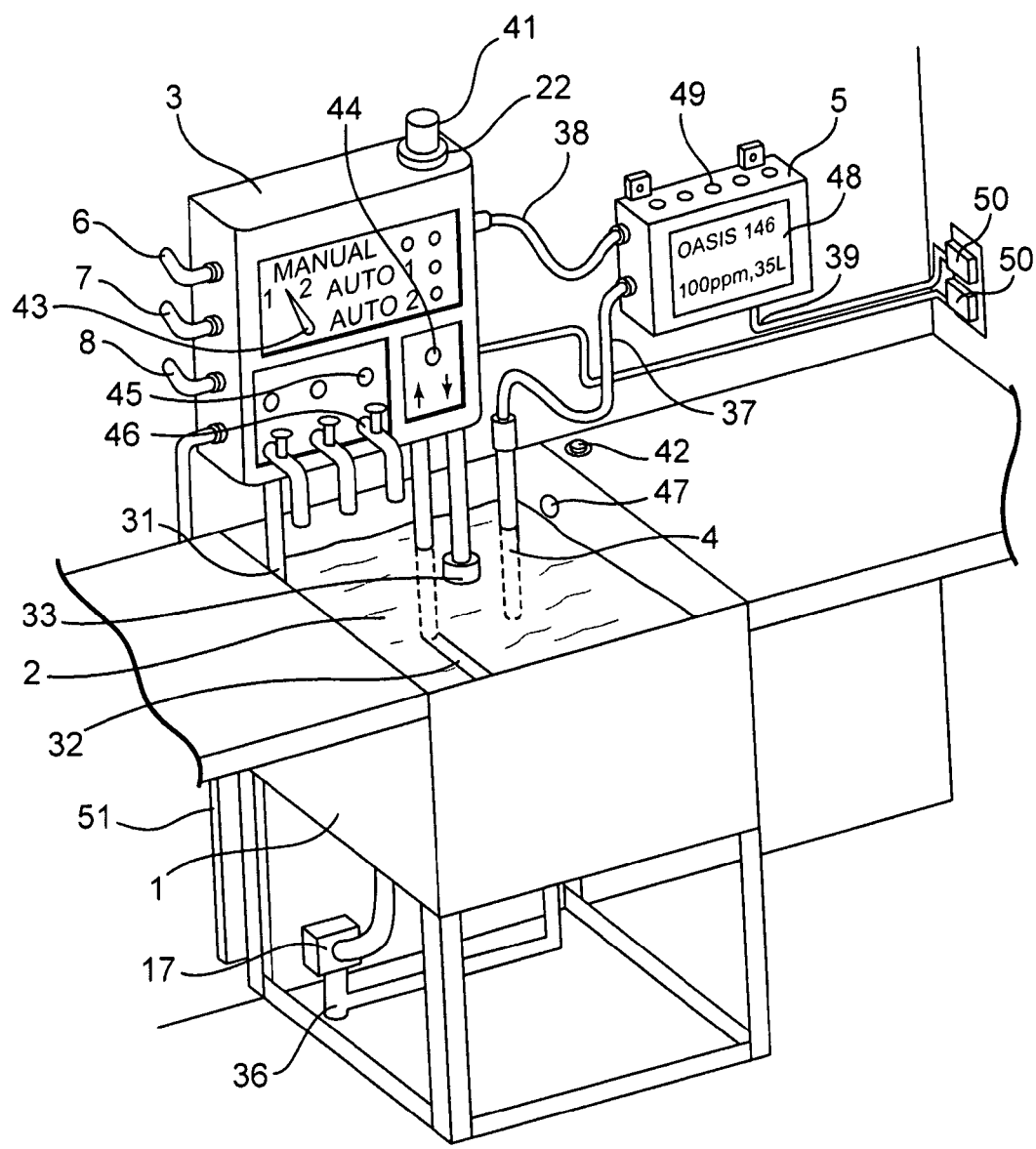
FIG. 1B shows a sanitizing system with a fluorometric sensor for sanitizer concentration measurements in a container, such as a tank.

FIG. 1A shows a block diagram of a fluorometric sensing system 1000 for measuring chemical concentration in a liquid or gaseous sample concentration. The system includes a sample solution tank 1 which contains a sample solution 2, an automated dispenser 3 for dispensing water and sample into the tank 1 directly from a hot water inlet 6, a cold water inlet 7, a sample concentrate inlet 8 through electrical valves 9, 10, 11 respectively or through electrical valves 12, 13, 14 after mixing in a mixing device 20 placed inside of the automated dispenser 3 to mix the dispensed water and sample, a fluorometric sensor 4, which can be placed inside of a test chamber 21 or directly in the sanitizing solution tank 1 (which position is shown in FIG. 1A as reference numeral 4a), a controller 18 that controls the automated dispenser 3, a pump 19 which takes the sample solution 2 from the solution tank 1 through an input pipe 32 to pump it through a heater 24, electrical valves 15, 16 and returns the sample solution to the solution tank 1 through a filter 33 for filtering out any possible contaminations, flow sensors 25-29, a level sensor 31 that senses a solution level in the tank 1, a pressure sensor 34 that senses whether the filter 33 becomes clogged with contaminations, an overflow pipe 35 that releases overfill solution to a drain 36, a valve 17 that releases the sanitizing solution 2 to the drain 36 when the solution should be replaced for contamination of detergent, for temperatures out of a specified range, or for having a high turbidity, a sensor cable 37 that connects the sensor 4 to a display unit 5, an output cable 38 that outputs the reading the display unit 5 to the controller 18, a display unit power supply cable 39, and a dispenser power supply cable 40. The heater heats the solution 2 if a temperature sensor 30 senses the temperature lower than a preferred temperature. The fluorometric sensor 4 can be placed inside the test chamber 21 inside the automated dispenser 3 (positioned as shown on the top right side of FIG. 1A) or can be placed into the tank 1 (positioned as shown 4a at bottom right side of FIG. 1A). The test chamber 21 has a lid 22 and an o-ring 23 to seal the fluorometric sensor 4 therein. FIG. 1B shows a sanitizing system with a fluorometric sensor for sample concentration measurements in the tank 1 where it is secured with a bracket 42. Alternatively, the fluorometric sensor 4 is mounted to the tank 1 on a sensor mounting bracket 42 (outside of the dispenser 3 as shown in FIG. 1B). When the fluorometric sensor 4 is placed in the tank 1 (as shown 4a at bottom of FIG. 1B), a plug 41 is inserted in the test chamber 21 and sealed with the lid 22 and the o-ring 23, inside of the automated dispenser 3. The sample solution 2 may be used to clean kitchen ware in a restaurant, in a laundry facility, be dispensed into a cleaning solution container, etc.

The controller 18 may have fixed hardware design and/or is software-driven. The testing parameters complies with ISO 7816 ATR (answer to reset) comparison table, commands, and appropriate responses, so as to be added and altered, as needed to cope with different needs of a user. The automated dispenser 3 has an operation mode switch 43 for a user to adjust among four operation modes: a manual mode 1, a manual mode 2, an auto mode 1 and an auto mode 2. The manual mode 1 and the auto mode 1 work when the fluorometric sensor 4 is set in the test chamber 21, while the manual mode 2 and the auto mode 2 work when the fluorometric sensor 4 is set in the tank 1. The pump 19 (FIG. 1A) can be automatically started by the controller 18 based upon low temperature readings under the AUTO modes, or by an user through pressing a pump manual start button 44 to circulate the solution from the input pipe 32 to the automated dispenser 3 and then through the filter 33 to the tank 1 under the Manual modes. In the manual modes, the user can press one of faucet buttons 45 to let water and/or sample through the hot water inlet 6, the cold water inlet 7, and the sample concentrate inlet 8 into the automated dispenser 3 through the electrical valves 9, 10, 11 and then through the respective faucets 46 into the tank 1. An overflow pipe insert 47 is provided for inserting the overflow pipe 35. The display unit 5 includes a display 48 and five indication LEDs 49. A cable 51 connects the controller 18 and the electrical valve 17 for draining the solution 2. The manual mode 1 and 2 allow manually adjusting temperature and concentration using data from the display 48 and manually pressing buttons on the automated dispenser 3. In the auto mode 1 and 2, the controller 18 receives data from the flow sensors 25-29, a temperature sensor 30, a level sensor 31, a pressure sensor 34 and automatically operates with the valves 12-17, the heater 21 and the pump 19 to follow a programmed algorithm and maintain the solution temperature and concentration inside preset limits.

Figure 2A:
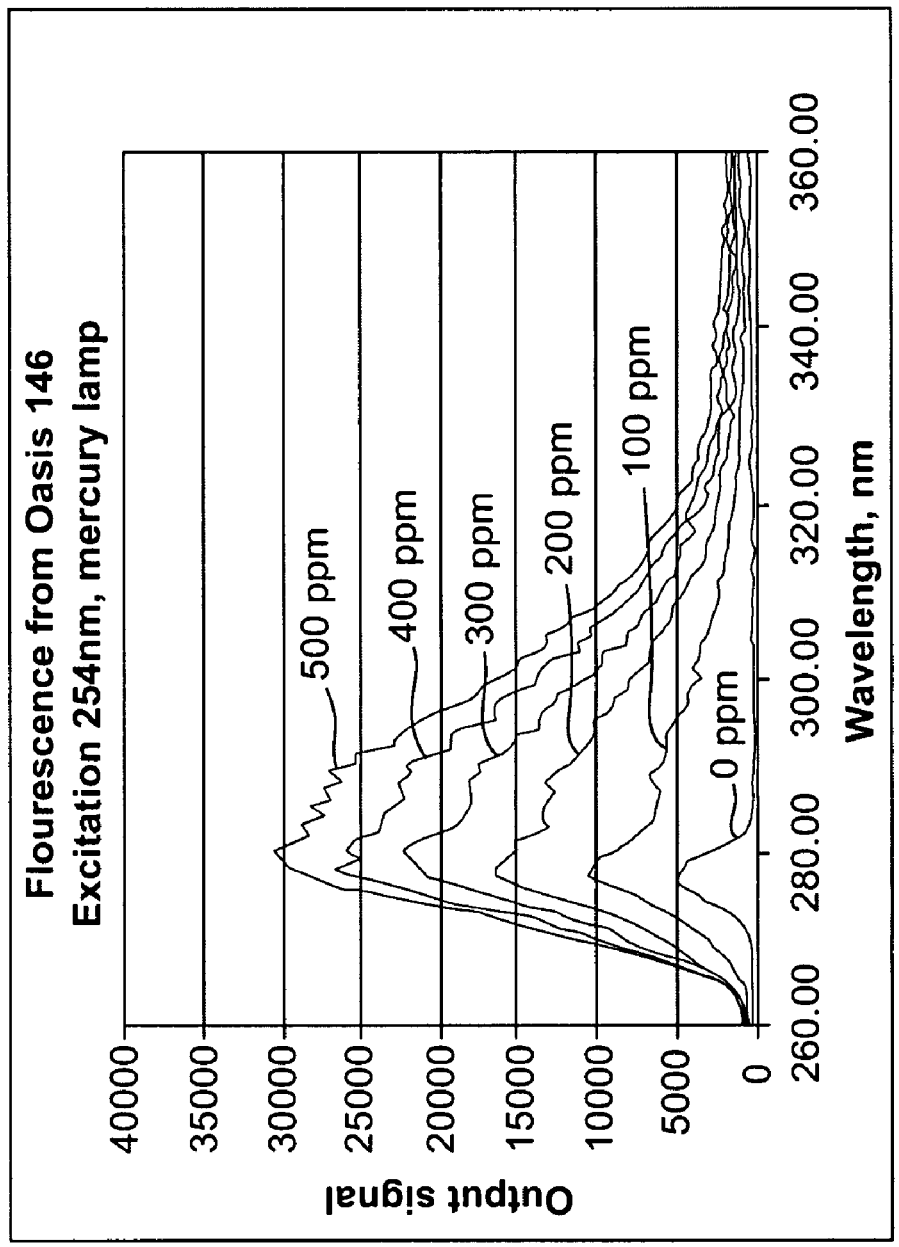
FIG. 2A shows a measured fluorescence spectra for an OASIS 146 MULTI-QUAT SANITIZER® (hereinafter "Oasis 146") with a UV lamp.
Figure 2B:
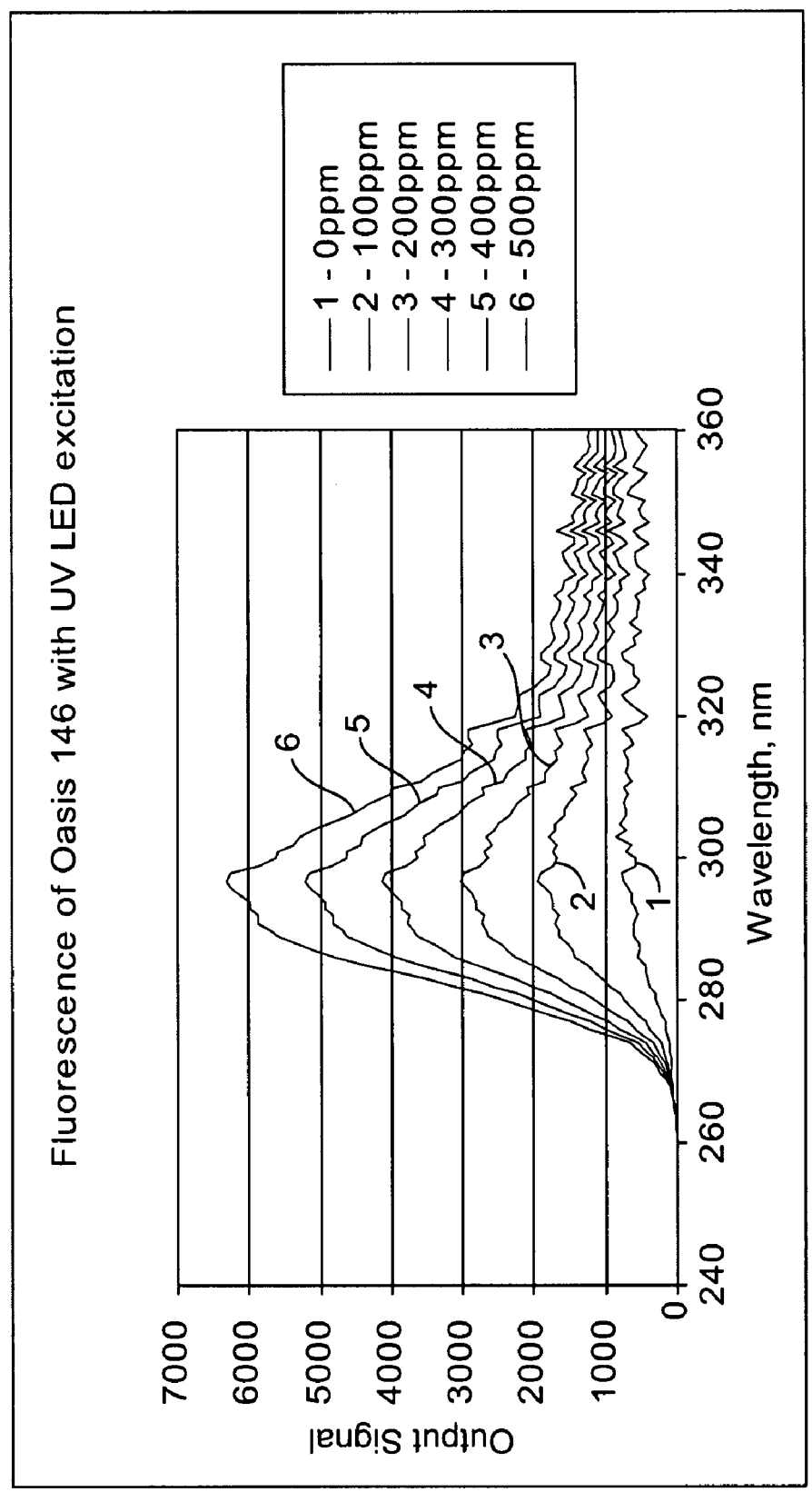
FIG. 2B shows spectral variations in fluorescence measurement for the same concentrations of the OASIS 146 with a UV LED.
Figure 2C:
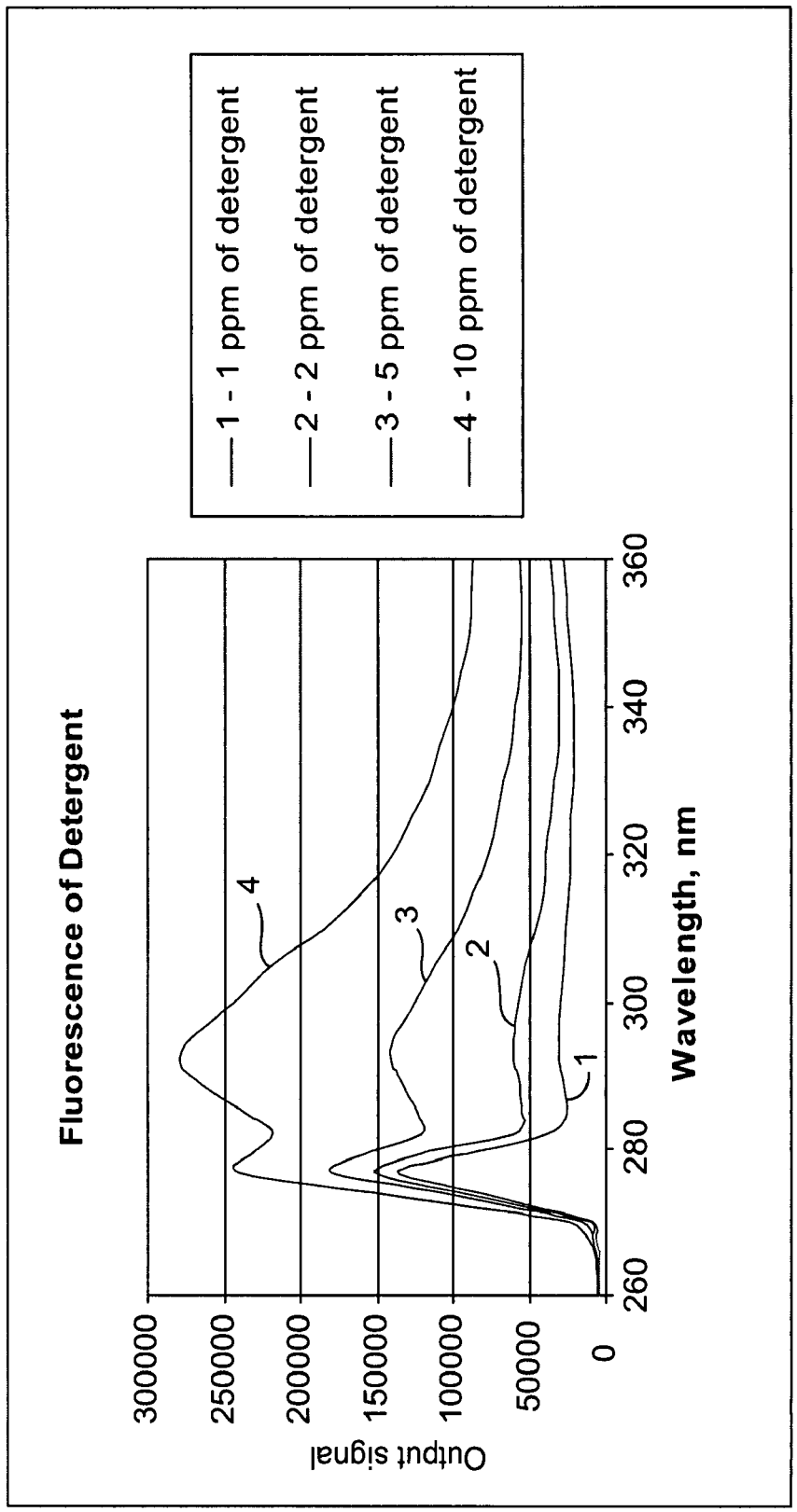
FIG. 2C shows a measured fluorescence spectra a Pan Max Ultra Liquid Dish Detergent®.
Figure 2D:
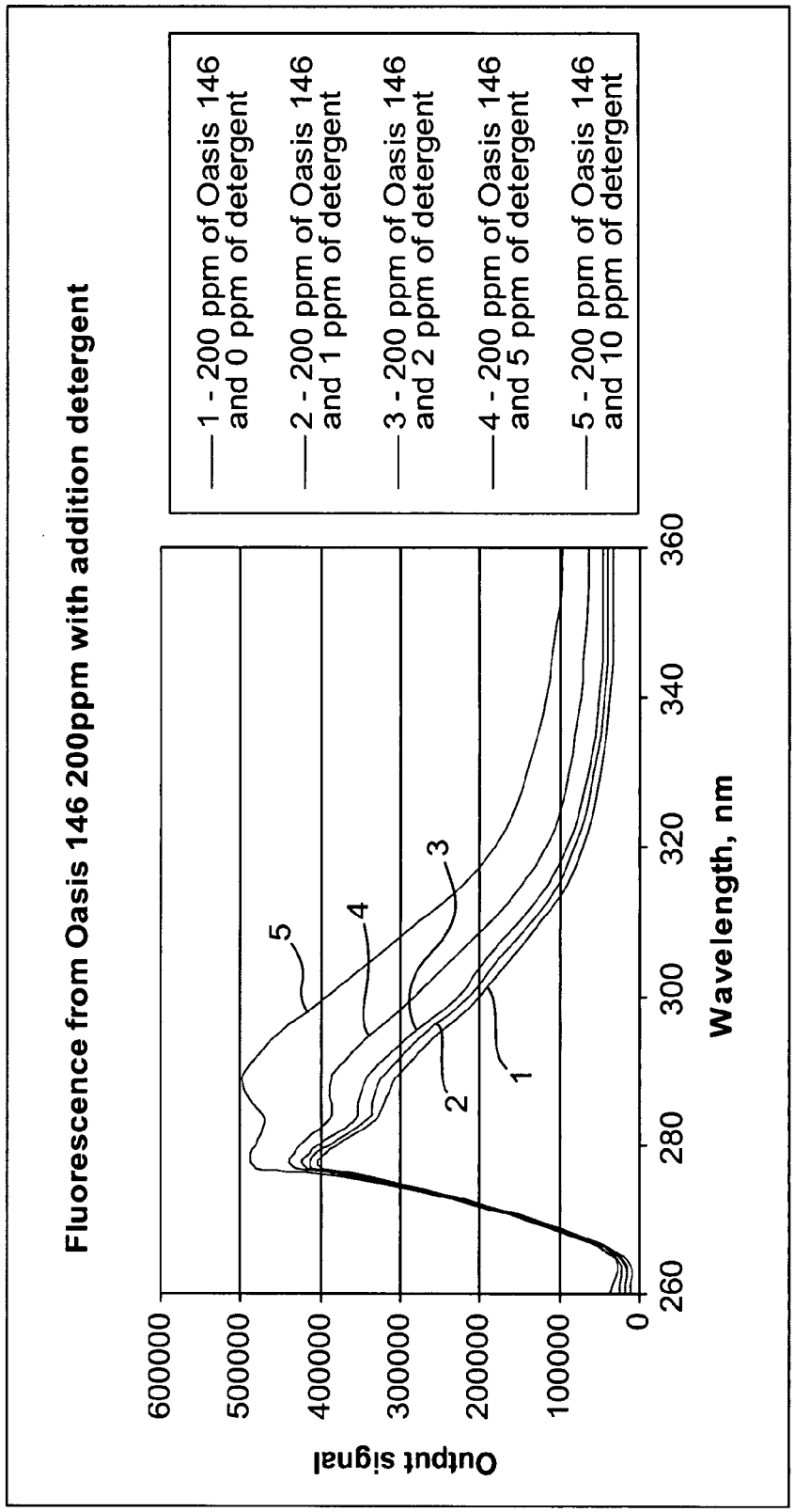
FIG. 2D shows a measured fluorescence spectra of the OASIS 146 and the detergent.

OASIS 146 MULTI-QUAT SANITIZER® by Ecolab Inc. (St. Paul, Minn.) (hereinafter referred to as "OASIS 146) is a mixture of alkyl dimethyl benzyl ammonium chloride and dialkyl dimethyl ammonium chloride. The alkyl units refer to carbon chains ranging from approximately 8 to 20 carbon units. The Oasis 146 quat is used against, for example, *Pseudomonas aeruginosa, Staphylococcus aureus* and *Salmonella choleraesuis*. Active components of the OASIS 146 absorb UV radiation in a range from 200 nm to 270 nm and produce fluorescence in a range from 265 nm to 330 nm. Different UV light sources can be used for fluorescence excitation. FIG. 2A shows measured fluorescence spectra of OASIS 146 for concentrations from 0 ppm to 500 ppm in a solution (with zero impact by detergents) with excitation at 254 nm using a low pressure mercury lamp. FIG. 2B shows measured fluorescence spectra for the same concentrations of the OASIS 146 excited at 255 nm with a UV LED. Sanitizing solutions with the OASIS 146 may be impacted by a variety of factors including soils and detergent compounds which are often used as a first cleaning agent in ware-washing applications. The measured fluorescent spectra of an example detergent (PAM MAX ULTRA LIQUID DISH DETERGENT by Ecolab Inc.) are shown at FIG. 2C. The fluorescence of the detergent is shifted to the longer UV wavelengths compared to the OASIS 146 fluorescence. FIG. 2D shows measured fluorescence spectra of samples having identical 200 ppm of the OASIS 146 and 0 ppm, 1 ppm, 5 ppm, 10 ppm of the detergent. According to present invention, two spectral ranges are selected to measure the OASIS 146 in presence of the detergent. The first range is from approximately 265 nm to 295 nm, and the second range is from approximately 295 nm to 340 nm. Those two ranges can be separated by optical UV interference filters such that concentrations of the OASIS 146 and the detergent can be calculated using a known calibration and a known intensity of fluorescent signal from the two spectral ranges. Another embodiment of the invention uses several glass filters to measure fluorescence from a combination of the first and second ranges (from approximately 265 nm to 340 nm) and from the second range (from approximately 295 nm to 340 nm). For example, one channel has a combination of 3 mm of UG11 glass with 2 mm of WG280 glass, and another channel has a combination of 3 mm of UG11 glass with 2 mm of WG295 glass.

Figure 3A:
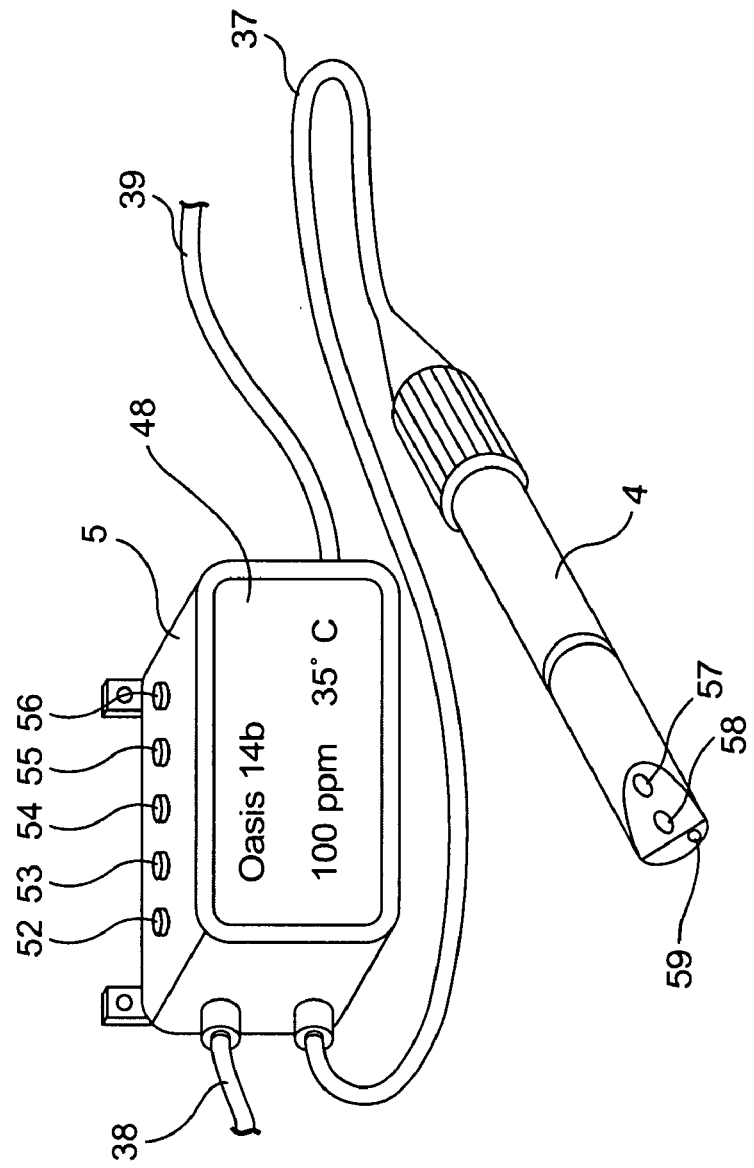
FIG. 3A shows an enlarged view of the fluorometric sensor in FIG. 1B with the wall mounted display unit in FIG. 1B.

FIG. 3A shows an enlarged view of the fluorometric sensor 4 with the wall mounted display unit 5. The five indication LEDs 49 includes a low concentration indicator LED 52, an overdosed solution indicator LED 53, a contaminated solution indicator LED 54, a normal operation indicator LED 55, and a low solution temperature indicator LED 56 which light up to warn the user of any occurrence of the respective abnormal situation. The fluorometric sensor 4 has a detector window 57, a light source window 58 and a temperature sensor insert 59 set on a substantially flat bottom surface thereof. The detector window 57 and the light source window 58 are set on a surface tilted away from the flat bottom surface about 45 degrees. Further details of the fluorometric sensor 4 are explained herein with respect to FIGS. 4-5.

Figure 3B:
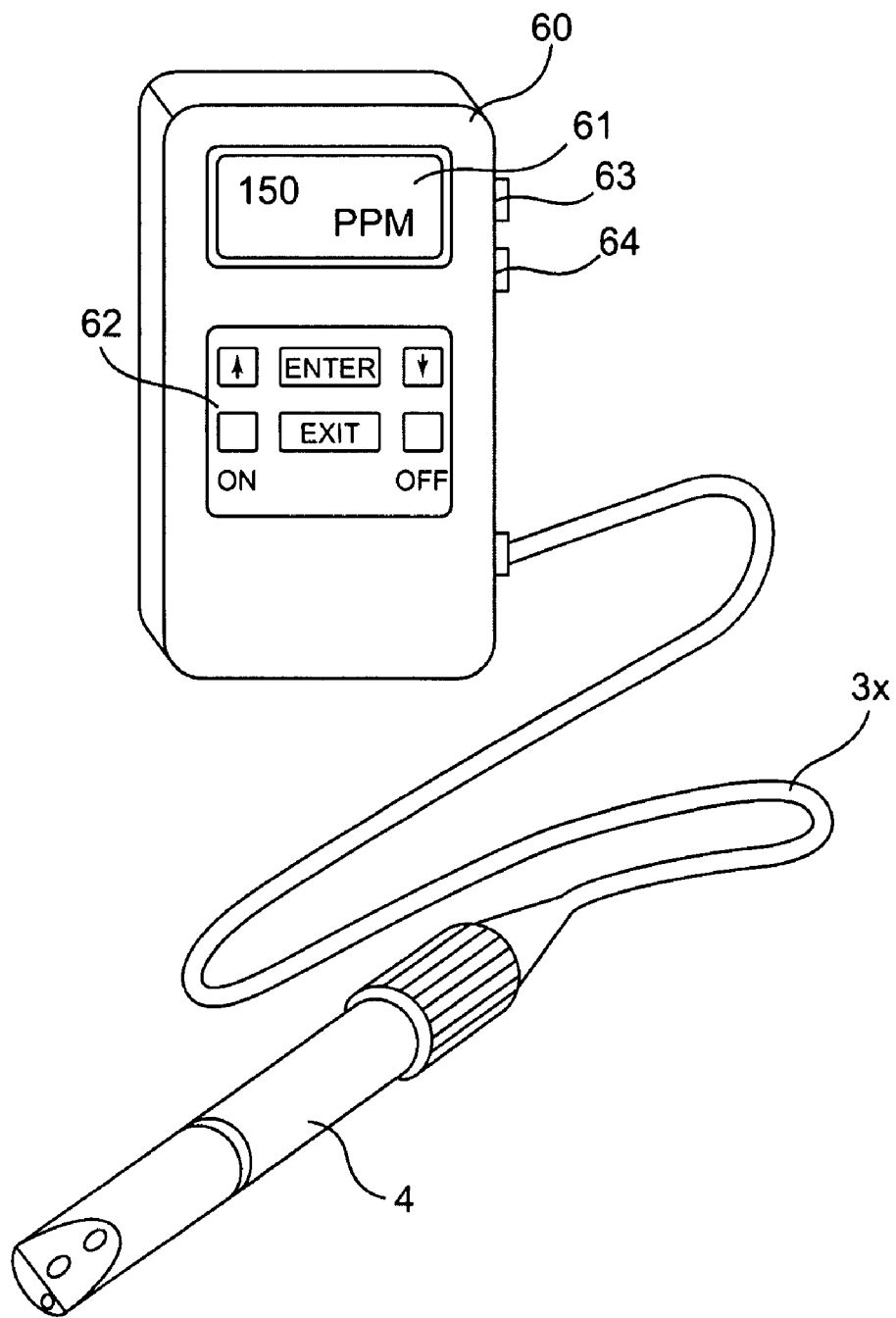
FIG. 3B shows a prospective view of another embodiment of the invention having a hand held display unit connected the fluorometric sensor in FIG. 1B.

FIG. 3B shows a prospective view of another embodiment of the invention having a hand held display unit 60 connected through the sensor cable 37 to the dip-fluorometric sensor 4. The hand held display unit 60 includes a display 61, a keypad 62, a DC power connector 63 and a communication connector 64. The display 61 is a vacuum florescent display or a LCD display. The hand held display unit 60 may connect to other external equipment through the communication connector 64 or wirelessly communicate with a computer. Through communication connector 64 or wireless communication, held display unit 60 may receive modified or updated operation or user data information.

Figure 4:
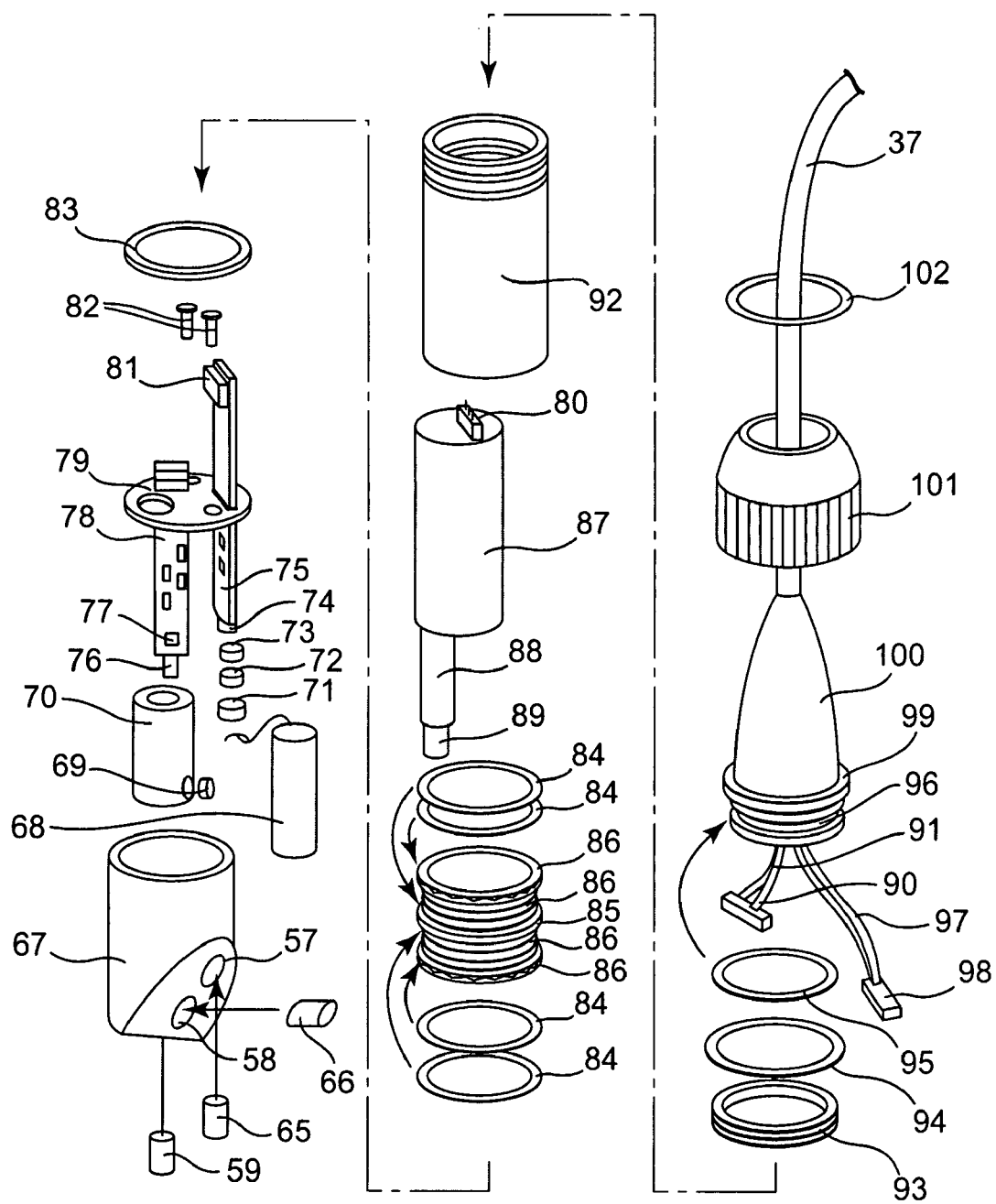
FIG. 4 shows an exploded view of the fluorometric sensor of FIG. 1B.
Figure 5A:
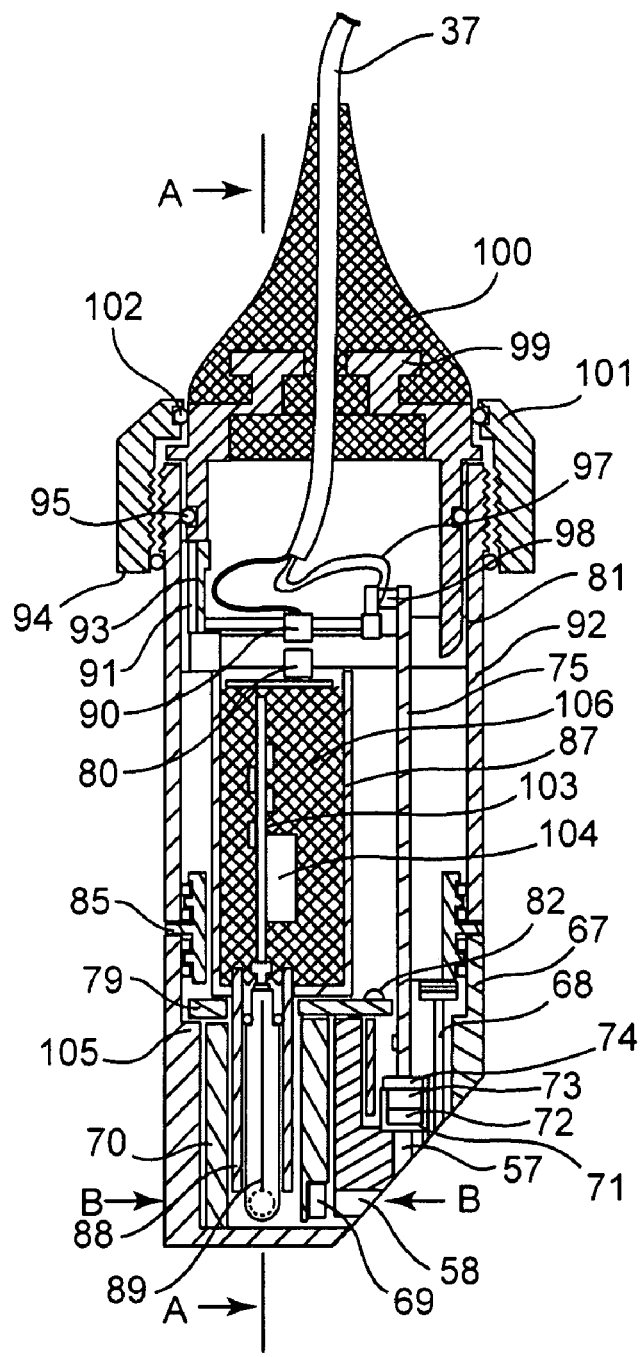
FIG. 5A shows a cross-sectional of the fluorometric sensor in FIG. 1B taken through a UV lamp and a detector channel UV photodiode.

FIG. 4 shows an exploded view of the fluorometric sensor 4. The fluorometric sensor 4 has a housing 92, which has a sensor cover 99 attached thereto through the interlocking between the threads on the outer surface of the housing 92 and the threads of a mounting nut 101. The sensor cover 99 has an O-ring groove 96 on its outer surface to interlock with a molded strain relief 100 which has the sensor cable 37 inserted therethrough. As shown in FIGS. 4 and 5A, an internal mounting washer 93 is provided between housing 92 and the sensor cover 99. A first external O-ring 94 is provided between a lower edge of the mounting nut 101 and the outer surface of the housing 92. An internal O-ring 95 is provided between an inner surface of the housing 92 and the sensor cover 99. A second external O-ring 102 is provided between the sensor cover 99 and an upper edge of the mounting nut 101. The housing 92 has a sensor head 67 snugly fitted thereto through a grounding insert 85. The grounding insert 85 has O-ring grooves 86 on its outer surface for accommodating four O-rings 84 and a grounding washer 83.

Inside the housing 92, there is a connection board 79 with a preamplifier board 75 and a reference board 78 soldered thereon. The connection board 79 has a hole thereon for a brass tube 88 inserting therethrough to protect UV lamp 89. The brass tube 88 is soldered into a housing of a shielded power supply 87. The housing of the shielded power supply 87 has a lamp power supply connector 80 on its external top surface. The lamp power supply connector 80 is connected with a connector 90 with a power supply cable 91.

FIG. 5A shows a cross-sectional view of the fluorometric sensor 4 taken through a UV lamp 89 and a detector channel UV photodiode 74. The cable 37 includes the power supply cable 91 and cable wires 97. As shown in FIG. 5A, the brass tube 88 accommodates the UV mercury lamp 89 therein and secures the lamp 89 with a lamp O-ring 105, to provide a light source chamber/channel. The housing of a shielded power supply 87 accommodates a power supply board 103 which has a high voltage transformer 104 and other components soldered thereon and filled with an insulation compound 106 therein. The connection board 79 is secured into the sensor head through two screws 82. The preamplifier board 75 is shielded in a preamplifier board shield 68. The preamplifier board 75 has a sensor connector 81 soldered on the top edge to be connected with a connector 98 with cable wires 97 connected thereto. The preamplifier board 75 has the UV photodiode 74 attached on the lower edge and covered by a detector filter cover 71. Two glass filters (WG280, UG-11) 72, 73 are provided in the detector filter cover 71 between the detector window 57 and the UV photodiode 74 and facing towards the detector window 57. An excitation filter (optional) 69 is provided on an excitation filter holder 70 surrounding the light source chamber and facing towards the light source window 58.

Figure 5B:
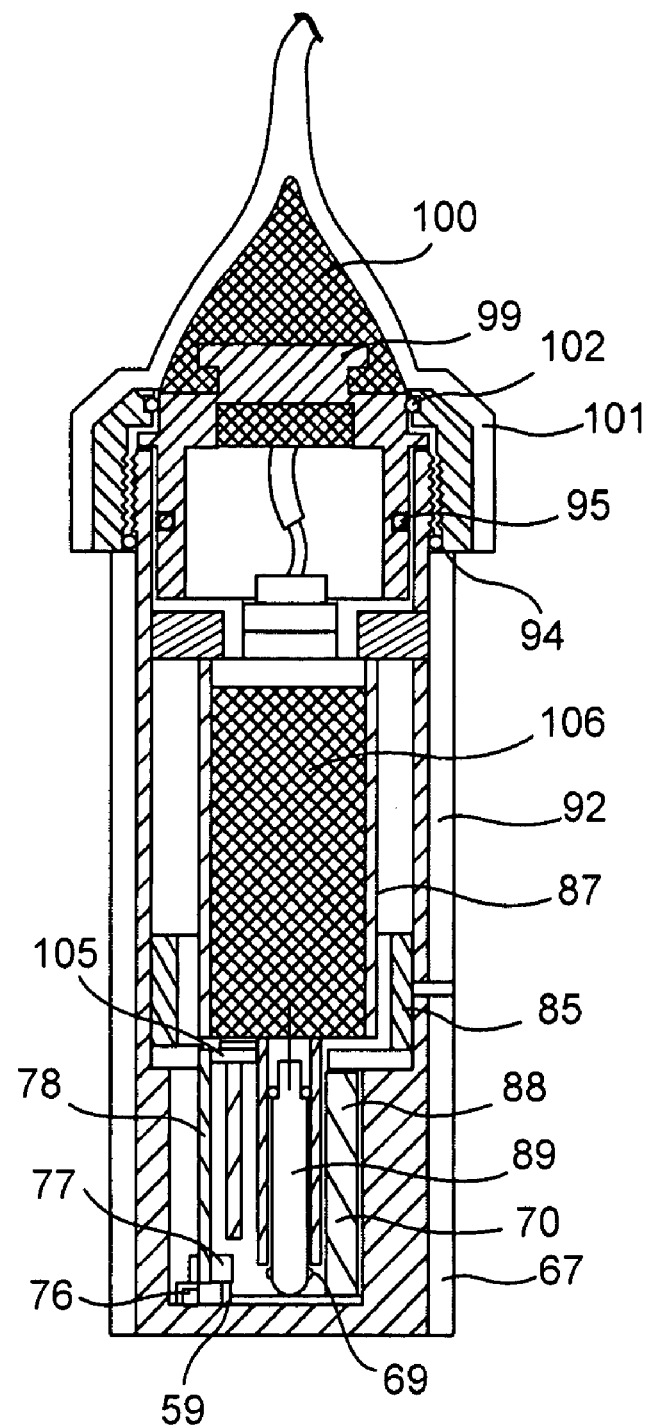
FIG. 5B shows a cross-sectional view of the fluorometric sensor in FIG. 5A taken through the UV lamp and a reference channel UV photodiode along a line A-A.
Figure 5C:
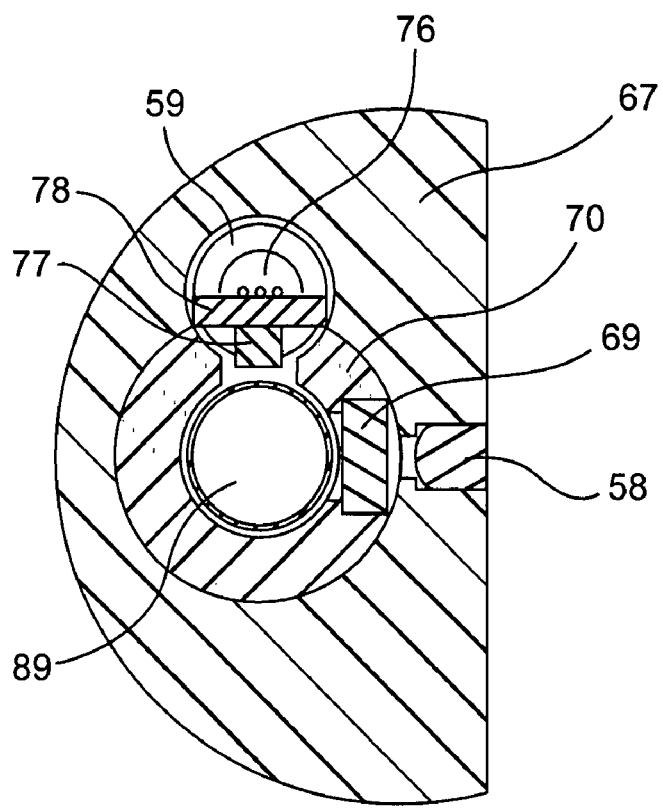
FIG. 5C shows a cross-sectional view of the fluorometric sensor in FIG. 5A taken through a line B-B.

FIG. 5C shows a cross-sectional view of the fluorometric sensor 4 shown in FIG. 5A taken through a line B-B. The light source chamber is enlarged in FIG. 5C. The excitation filter 69 is provided between the light source 89 and the light source window 58. The detector window 57 and the light source window 58 are sapphire prismatic lenses having spherical surfaces on one side and flat tilted surfaces on another side of a cylindrical body.

Figure 7:
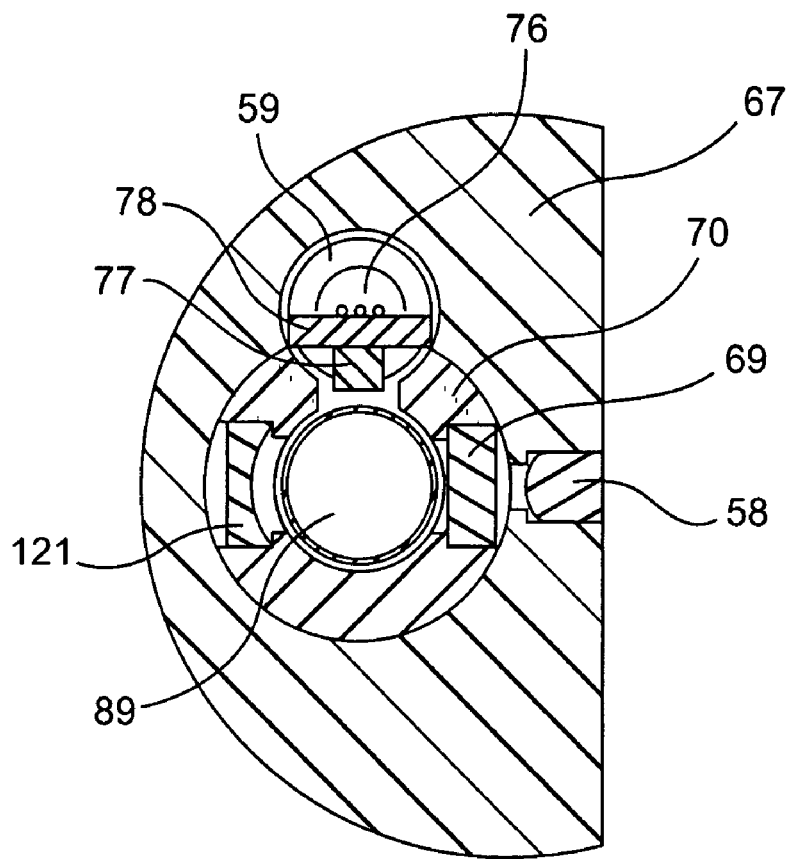
FIG. 7 shows an electrical block diagram of the embodiment of the invention depicted in FIG. 3A.

FIG. 7 shows another embodiment of the fluorometric sensor 4 adding a concave or flat mirror 121 into the filter holder 70 as well as opposite to the excitation filter 69 across the light source 89 to increase excitation irradiation by reflecting the light emitted from the UV lamp 89 towards the opposite side to the light source window 58 back towards the light source window 58. In one embodiment, the light source chamber/channel and the detector chamber/channel may have a cylindrical shape.

The UV lamp 89 may be a gas discharge lamp, a mercury lamp, a deuterium lamp, a metal vapor lamp, a light emission diode or a plurality of light emission diodes. Preferably, the ultraviolet lamp 89 may be a mercury low pressure lamp with main line at 254 nm (by BHK. Inc, Claremont Calif.) or a UV lamp such as a Krypton gas discharge lamp (by Hile Controls, Fla.). A light emission diode (model UV LED-255 by Photon Systems, Inc., Covina, Calif.) can be used as a light source. Optionally, an additional ultraviolet detector is used to monitor intensity of the ultraviolet lamp 89.

FIG. 5B shows a cross-sectional view of the fluorometric sensor 4 shown in FIG. 5A taken through the UV lamp 89 and a reference channel UV photodiode 77 along a line A-A. The reference board 78 has the UV photodiode 77 attached on the lower edge facing the UV lamp 89 and a temperature sensor 76 provided in the temperature sensor insert 59 and connected to another side of the reference board 78.

Figure 6A:
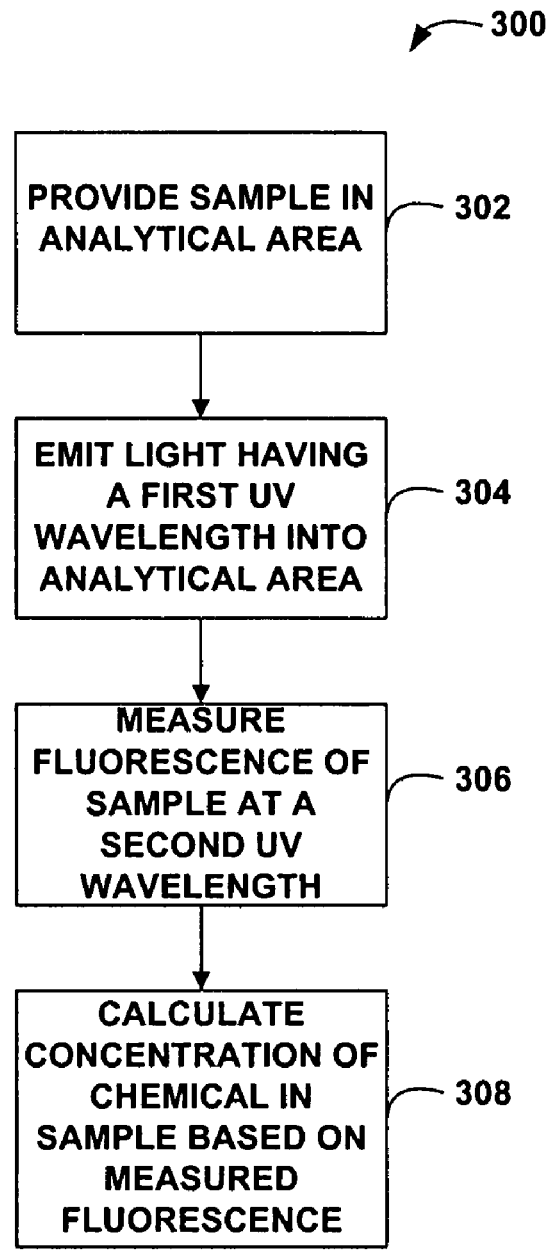
FIG. 6A is a flowchart illustrating the process by which a fluorometric sensor determines the concentration of chemical(s) in a sample.

FIG. 6A is a flowchart illustrating the process (300) by which the fluorometric sensor determines the concentration of a chemical in a sample. The sensor measures a fluorescent light emission of the active molecule that is proportional to the actual concentration of chemical(s) in a sample. A sample containing a chemical that exhibits fluorescent characteristics is provided in an analytical area of the sensor (302). The sensor emits an ultraviolet (UV) light having a first UV wavelength through the analytical area (304). The sensor measures the fluorescence emission of the sample at a second UV wavelength (306). The sensor includes a controller (115 in FIG. 6B, for example) that calculates the concentration of the chemical in the sample based on the measured fluorescence emission (308). The first wavelength may be in the range of 245-265 nm. The second UV wavelength may be in the range of 265 nm to 340 nm. The sensor may also measure a reference fluorescence emission of the sample at the first wavelength. The sensor may also measure a fluorescence emission of a zero solution having zero concentration of the chemical. In that case, the concentration of the chemical in the sample may be calculated based on the calculated difference in the measured fluorescence emission of the sample containing the chemical and the measured fluorescence emission of the zero solution. The concentration of the sample may also be calculated based on a calibration constant determined for known concentrations of the chemical in a calibration sample.

For example, when using ultraviolet fluorometric sensing system having a mercury lamp producing a UV radiation at 254 nm, sample concentrations may be evaluated based upon the signals from two UV detectors. A first detector (fluorescent detector) measures a fluorescent value for the wavelength 280 nm±15 nm (range from 265 nm to 295 nm) and a second detector (reference detector) measures an intensity of UV excitation at the wavelength 254 nm. The calculation uses the following equations:

$$C = K_X (I^S_{280}/I^S_{254} - I^0_{280}/I^0_{254})$$

where C—an actual concentration of a chemical X (for example, a surfactant, an antimicrobial agent, etc) in a sample solution;

$K_X$—a calibration coefficient;

$I^S_{280}$—an output signal from the first detector for a sample solution;

$I^S_{254}$—an output signal from the second detector for a sample solution;

$I^0_{280}$—an output signal from the first detector for a zero solution (i.e., a solution with zero concentration of the chemical); and $I^0_{254}$—an output signal from the second detector for a zero solution.

$$K_X = C_{CALIBR}/(I^{CALIBR}_{280}/I^{CALIBR}_{254} - I^0_{280}/I^0_{254})$$

where $C_{CALIBR}$—a concentration of the chemical in a calibration solution;

$I^{CALIBR}_{280}$—an output signal from the first detector for the calibration solution; and $I^{CALIBR}_{254}$—an output signal from the second detector for the calibration solution.

When the chemical is quat, $$C_{QUAT} = K_{QUAT}(I^S_{280}/I^S_{254} - I^0_{280}/I^0_{254}).$$

Figure 6B:
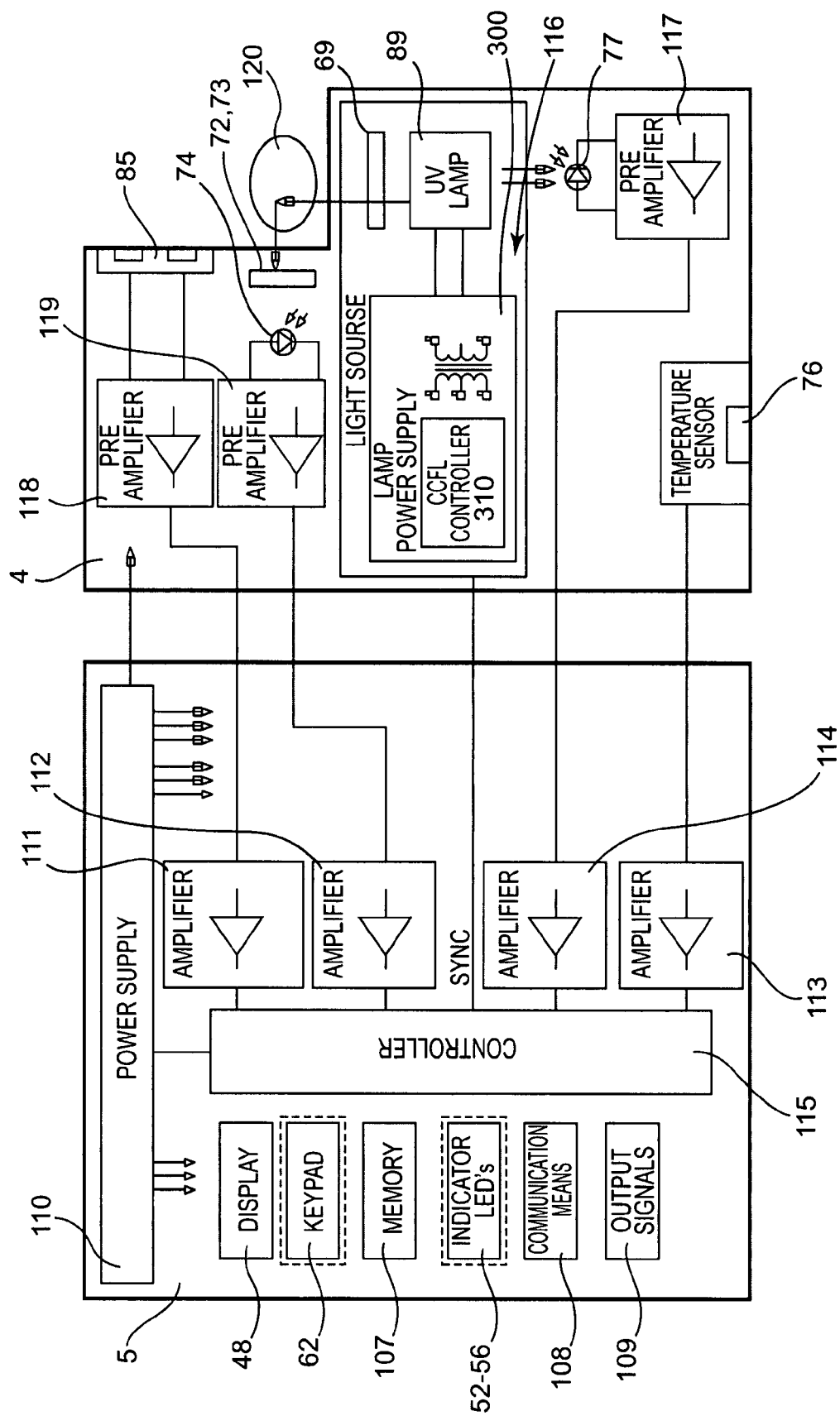
FIG. 6B shows a cross-sectional view of a fluorometric sensor similar to the one in FIG. 5A with an optional concave mirror to increase UV excitation beam intensity.

FIG. 6B shows an electrical block diagram of the embodiment of the invention depicted in FIG. 3A. The display unit 5 includes a controller 115, connected to a power supply 110, amplifiers 111-114, the display 48, the keypad 62, a memory 107, the indicator LEDs 52-56, communication means 108, and output means 109. The power supply 110 also supplies power to other components in the display unit 5 and the fluorometric sensor 4, except the light source 116. The light source 116 is powered by a lamp power supply 300 which is controlled by a compact fluorescent light bulb controller (CCFL) 310.

As mentioned above, controller 115 calculates the fluorescence values for one or more wavelength ranges from 265 nm to 340 nm and determines the concentration of the agent using the calculated difference in the fluorescence values for one or more wavelength ranges from 265 nm to 340 nm and calibration constants found for known concentrations of the agent. Operation instructions for controller 115 may be stored in memory 107. In that respect, memory 107 may be a computer-readable medium comprising program instructions that cause controller 115 to provide any of the functionality ascribed to them, and perform any of the methods described herein. Controller 115 may also store the raw fluorescence data obtained by the photodiode(s) and other pertinent data in memory 107. Controller 115 may also store any calculated fluorescence values and/or concentration data in memory 107.

The controller 115 sends synchronization signal "sync" to the CCFL controller 310 to coordinate operation of the fluorometric sensor. A UV light emits from the UV lamp 89 passes through the excitation filer 69 (e.g., a UV short-pass filter) and an optional focusing member 58 (FIG. 5A) to an analytical area 120. The UV short-pass filter 69 is placed in the output of a mercury lamp to transmit UV radiation for a mercury spectral line 254 nm but reject UV radiation with longer wavelengths. Molecules of active compounds of the sample, which are present in the analytical area 120, absorb UV radiation with a first wavelength and produce UV fluorescence in a second wavelength range. The intensity of the fluorescence is proportional to concentrations of those active molecules. The UV fluorescence passes the glass filter WG280 72 and the glass filter UG11 73 and reaches the detector channel UV photodiode 74. The glass filter WG280 72 and the glass filter UG11 73 transmit the fluorescence with wavelengths from 265 nm to 320 nm and absorb UV radiation for a mercury spectral line 254 nm, which is scattered from the analytical area 120 and can have an intensity higher than a fluorescent signal. The photodiode 74 converts the received UV fluorescence into an electrical signal which is then amplified by a preamplifier 119 and the amplifier 112 before reaching the controller 115.

The UV light emitted from the UV lamp 89 also reaches the reference channel UV photodiode 77. The photodiode 77 converts the received light into an electrical signal, which is then amplified by a preamplifier 117 and the amplifier 114 before reaching the controller 115. The temperature sensor 76 collects a temperature signal which is then amplified by the amplifier 113 before reaching the controller 115.

The grounding insert 85 collects a conductivity signal, which has a high conductivity value when the grounding insert 59 for the temperature sensor 76 and the grounding insert 85 both are immersed in water and which has a low conductivity value when one of inserts 59 or 85 is not immersed in water. The conductivity signal is then amplified by a preamplifier 118 and by amplifier 111 before reaching the controller 115. The controller 115 measures the conductivity signal and monitors the UV lamp according to a programmed algorithm. When the fluorometric sensor is immersed in a solution, the conductivity signal is high, the controller 115 turns power on for the UV lamp, and the fluorometric sensor automatically starts measurements. When fluorometric sensor is taken out of the solution, the controller 115 turns the power off for the UV lamp thereby decreasing power consumption and extending the lamp life.

Figure 8:
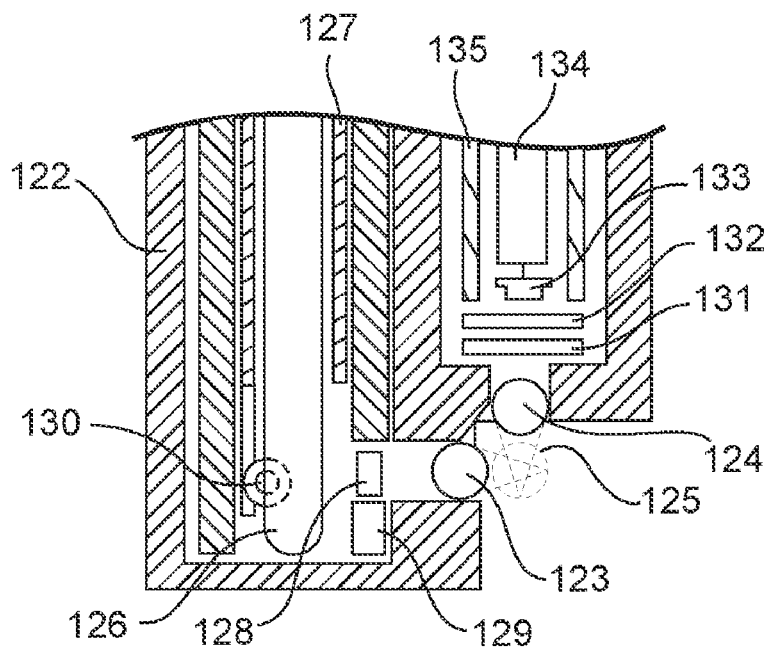
FIG. 8 shows a sensor head with a 90-degree geometry and using glass filters and sapphire ball lenses.

FIG. 8 shows a sensor head 122 which has 90 degree geometry using glass filters and sapphire ball lenses, rather than the sensor head 67 have a 45 degree tilted bottom surface as shown in FIG. 5A. The sensor head 122 uses a sapphire ball 123 as the light source chamber window 58 as well as focusing means, and uses another sapphire ball 124 as the detector window 57 as well as focusing means to provide an analytical area 125. The sapphire balls 123, 124 are standard optical components in place of custom-made prismatic lenses 57, 58. The other optical components in this embodiment are adjusted according to the deployment of the sapphire balls 123, 124 into a UV lamp 126, a brass tube 127, an excitation filter 128 (i.e., a short-pass UV filter), a filter holder 129, a reference diode 130, a glass filter UG11 131, a glass filter WG280 132, a UV diode 133, a preamplifier board 134 and a shield 135. Those parts are identical with or similar to those shown in FIG. 5A.

Figure 9:
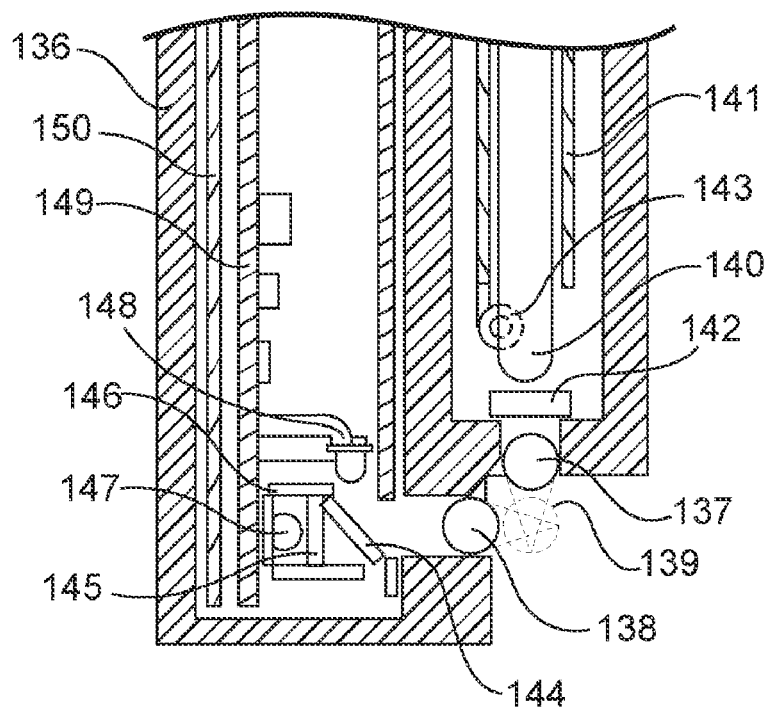
FIG. 9 shows a sensor head modified from the sensor head in FIG. 8.

FIG. 9 shows a sensor head 136, which is a modification of the fluorometric head 122 of FIG. 8 which swaps the positions of the detector chamber and the light source chamber and provides a turbidity channel within the detector chamber. The sensor head 136 uses a sapphire ball 137 as the light source chamber window as well as focusing means, and uses another sapphire ball 138 as the detector window as well as focusing means to provide an analytical area 139. In this embodiment, the light source chamber uses excitation filter 142, which has identical optical parameters with the excitation filter 128, along with an UV lamp 140, a brass tube 141 and a reference diode 143. A 45-degree dichroic mirror 144 is provided to separate the fluorescence coming from the analytical area 139 from UV radiation scattered from the analytical area 139. The UV radiation from the lamp 140 passes through the excitation filter 142 and the ball lens 137 to the analytical area 139. The scattered UV radiation from the analytical area 139 has an identical wavelength with the excitation UV radiation, and the dichroic mirror 144 reflects it toward the turbidity channel photodiode 148. The fluorescence form the analytical area 139 has different wavelengths from the excitation UV radiation, and it passes through the dichroic mirror 144 to an emission filter 145 and then reaches a fluorescent channel photodiode 147. The emission filter 145 and the dichroic mirror 144 are positioned in an optical path between the UV detector 147 and the ball lens 138, and the UV photodiode 148 is positioned perpendicular to the optical path and directed toward a center of the dichroic mirror 144

The emission filter 145 and the dichroic mirror 144 are supported by an emission filter holder 146. The embodiment also has a preamplifier board 149 and a shield 150.

Figure 10A:
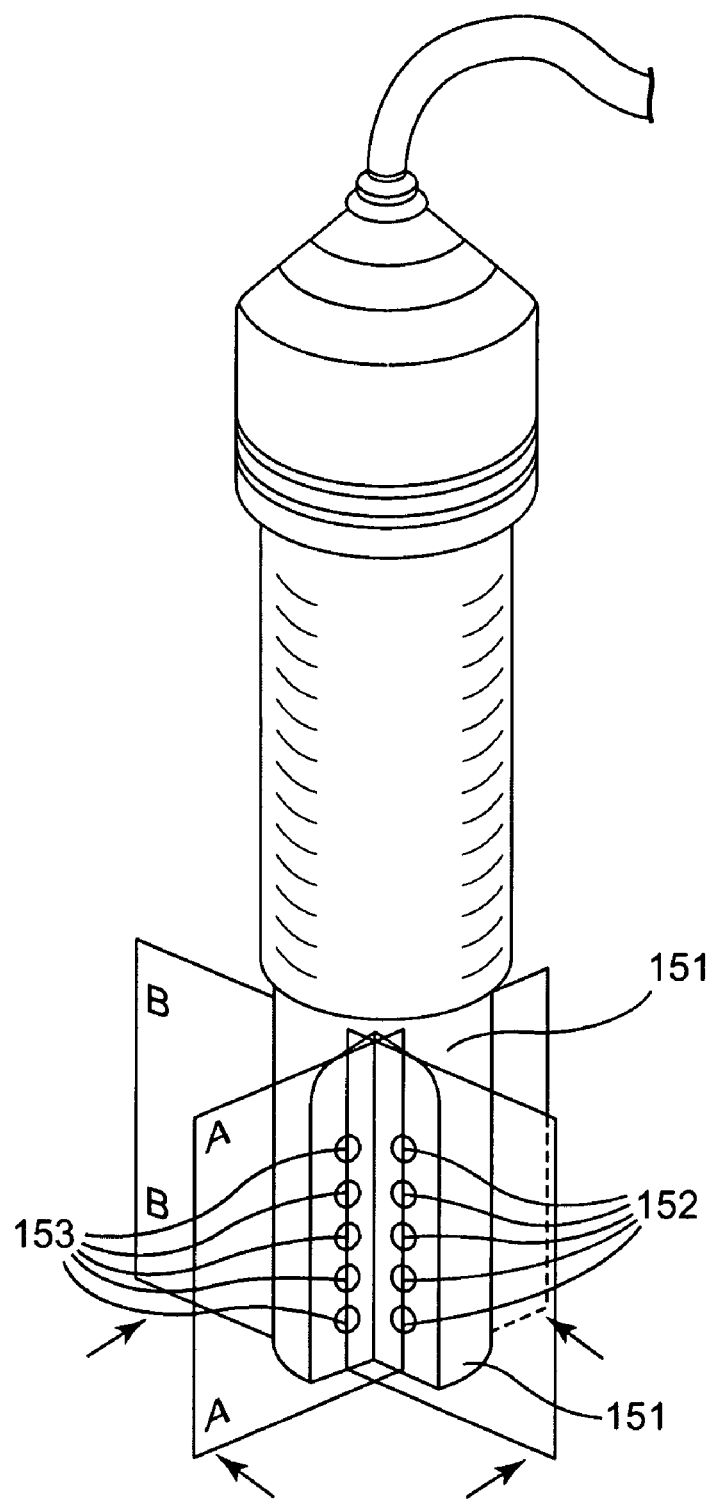
FIG. 10A shows a sensor head modified from the sensor head in FIG. 8 or FIG. 9 with multiple wavelength fluorescence detectors housed therein.
Figure 10B:
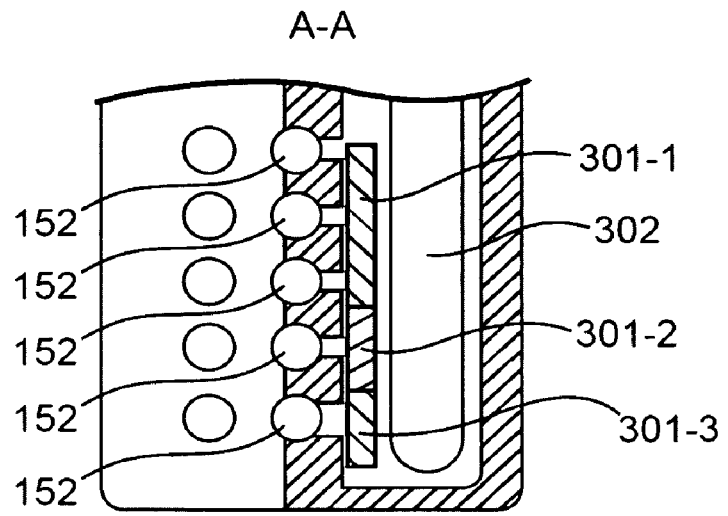
FIG. 10B shows a cross-sectional view of the sensor head in FIG. 10A taken through the light source window, UV lamp and excitation filters along a plane A-A.

FIG. 10A shows another embodiment of a fluorometric sensor with multiple wavelength fluorescence detectors housed in a sensor head 151. Each of the detectors has a light source window 152 and a detector window 153, which are located in a 90 degrees cutout in the sensor head 151. Therein all light source windows optically communicate with one gas discharge lamp and each of them forms an illuminated analytical area in front of a corresponding detector window. FIG. 10B shows a cross-sectional view of the sensor head 151 in FIG. 10A taken through the light source windows along a plane A-A. An optical filter 301-1 and optional optical filters 301-2 and 301-3 are located between a gas discharge lamp 302 and the light source windows 152 (which are sapphire ball lenses). In the embodiment shown in FIG. 10B, the gas discharge lamp 302 is a mercury lamp, the optical filter 301-1 is a UV short pass filter for transmitting radiation at 254 nm, the optical filter 301-2 is a narrow band UV filter for transmitting radiation at 296 nm, and the optical filter 301-3 is a narrow band UV filter for transmitting radiation at 365 nm. The combination of three wavelengths 254 nm, 296 nm and 365 nm allows the fluorometric sensor to measure many substances which have fluorescence under the excitation in the UV range.

Figure 10C:
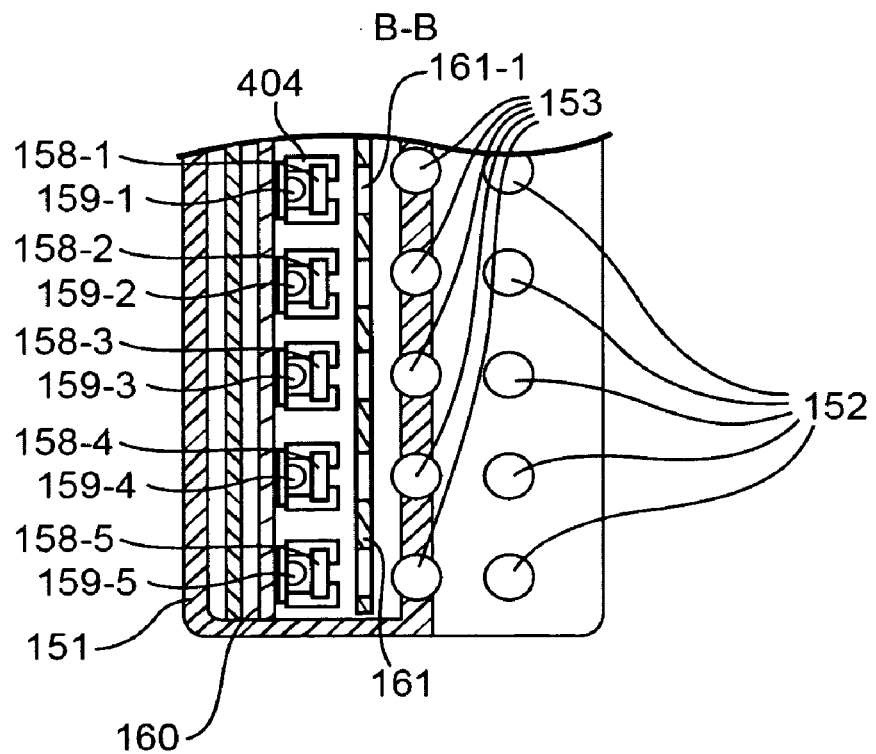
FIG. 10C shows another cross-sectional view of the sensor head in FIG. 10A taken along a plane B-B.

FIG. 10C shows a cross-sectional view of the sensor head 151 in FIG. 10A taken through the detector channels along a plane B-B. The photodiodes 159 are soldered on a preamplifier board 160 and shielded within a, shared shield 161. The shield 161 is made of a brass tube and has five holes 161-1 accommodating optical communication between the ball lens 153 and respective photodiodes 159. Each photodiode 159 has a filter holder 404 secured on the photodiode housing. Filters 158 for the channels installed in the filter holders 404 are optical interference filters or glass filters or a combination of such filters chosen to separate appropriate wavelength for each channel. In this embodiment, a filter 159-1 is a UG-5 glass filter, a filter 159-2 is a combination of UG-11 and WG-280 glass filters, a filter 159-3 is a combination of UG-11 and WG-305 glass filters, a filter 159-4 is a combination of UG-11 and WG-335 glass filters, and a filter 159-5 is a combination of BG-40 and GG-385 glass filters.

Figure 11A:
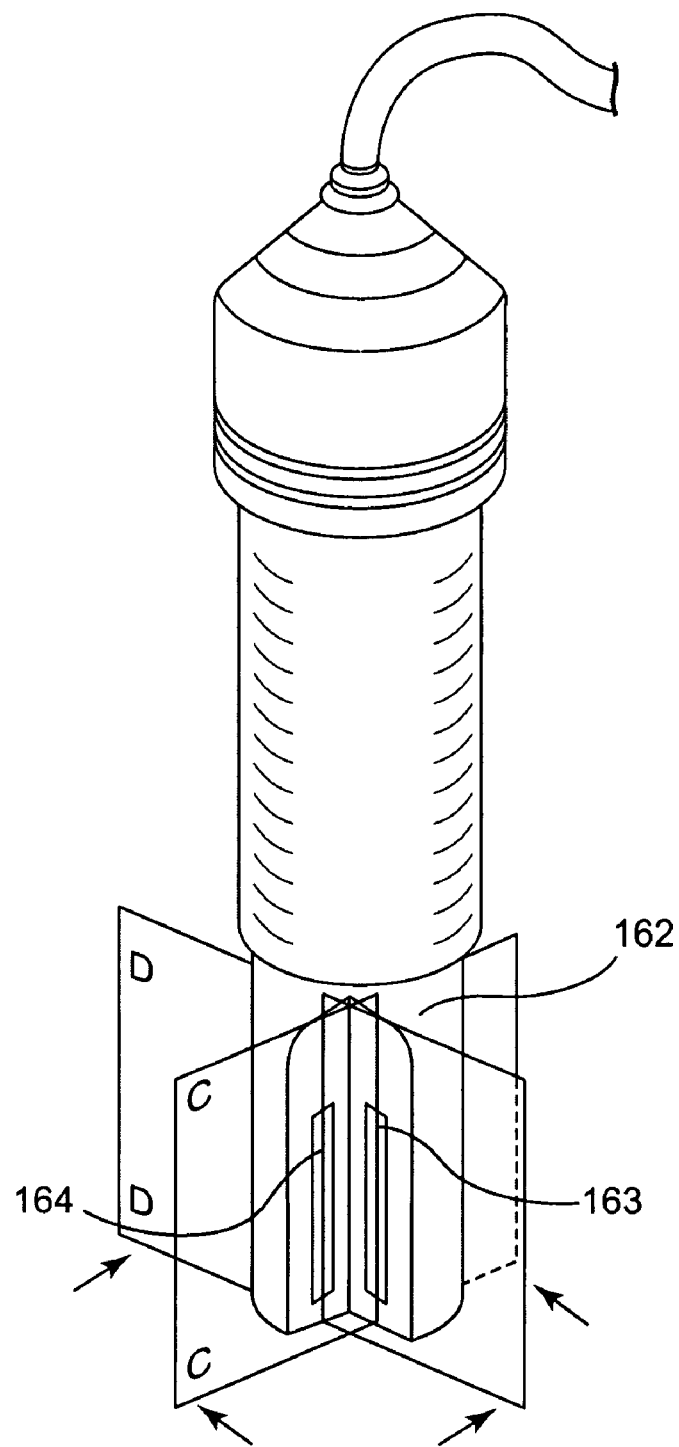
FIG. 11A shows a sensor head modified from the sensor head in FIG. 10A with a linear variable UV filter and a linear detector array housed therein.
Figure 11B:
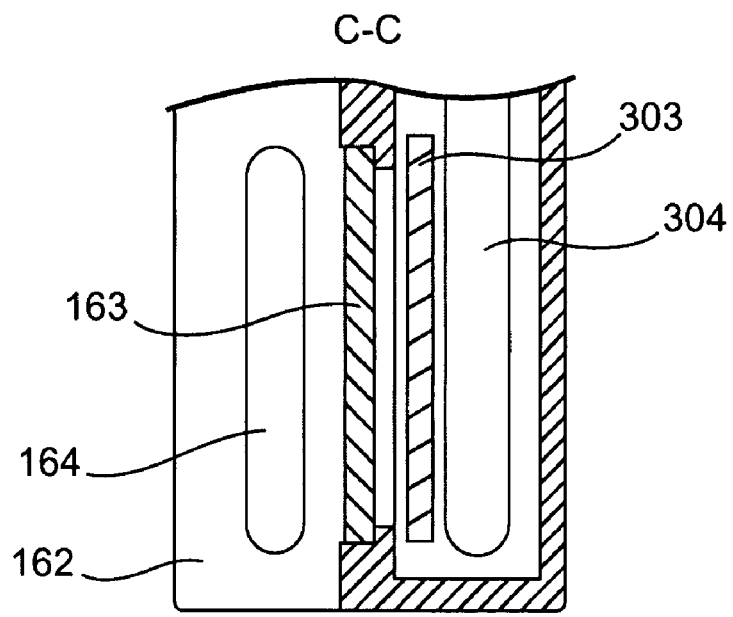
FIG. 11B shows a cross-sectional view of the sensor head in FIG. 11A taken through the light source window along a plane C-C.
Figure 11C:
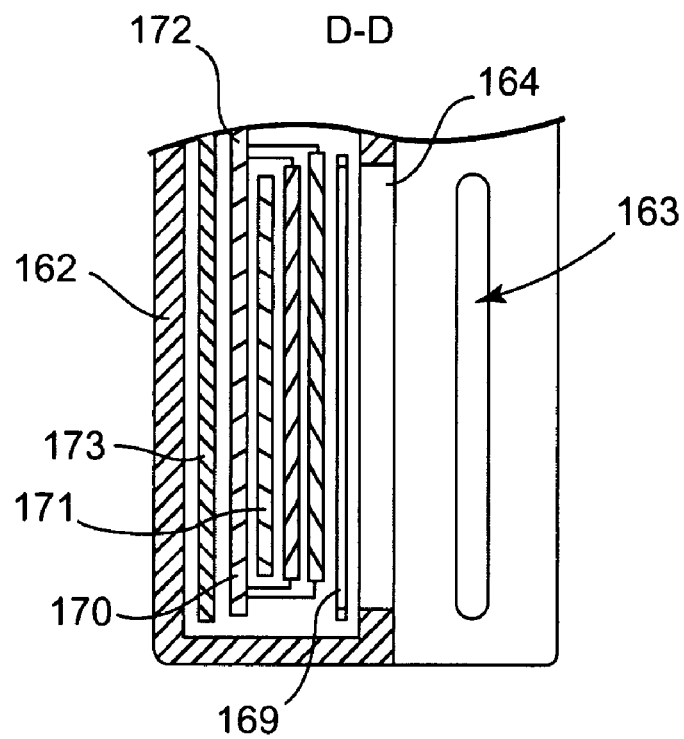
FIG. 11C shows a cross-sectional view of the sensor head in FIG. 11A taken through the detector window alone the plane D-D.

FIG. 11A shows a sensor head 162 which is a modification of the fluorometric head 151 in FIG. 10A. Rather than five separate light source windows 152 and five detector windows 153, this embodiment provides a shared light source window 163 and a shared detector window 164 made of a quartz or sapphire. FIG. 11B shows a cross-sectional view of the sensor head 162 in FIG. 11A taken through the light source window 163 along a plane C-C. A UV filter 303 made of UG-5 glass is placed between a UV lamp 304 and the light source window 163. The UV radiation from the UV lamp 304 passes through the UV filter 303 and the UV window 163 and produce a fluorescence in the analytical area in front of the detector window 164. FIG. 11C shows a cross-sectional view of the sensor head 162 in FIG. 11A taken through the detector window 164 along a plane D-D. A linear detector array 171 (S8865 by Hamamatsu, Japan) is soldered on a preamplifier board 172 for detecting multiple wavelength fluorescence from the analytical area. The linear ultraviolet filter 170 (LVF (UV) by JDSU, San Jose, Calif.) is placed between the linear detector array 171 and the shared detector window 164, with an additional glass filter 169 optionally sandwiched in-between. The fluorescent/turbidity channel is shielded within a shared shield 173. The shared shield 173 is made from a brass tube having a slit to accommodate optical communication between the analytical area and the linear detector array 171.

Figure 12:
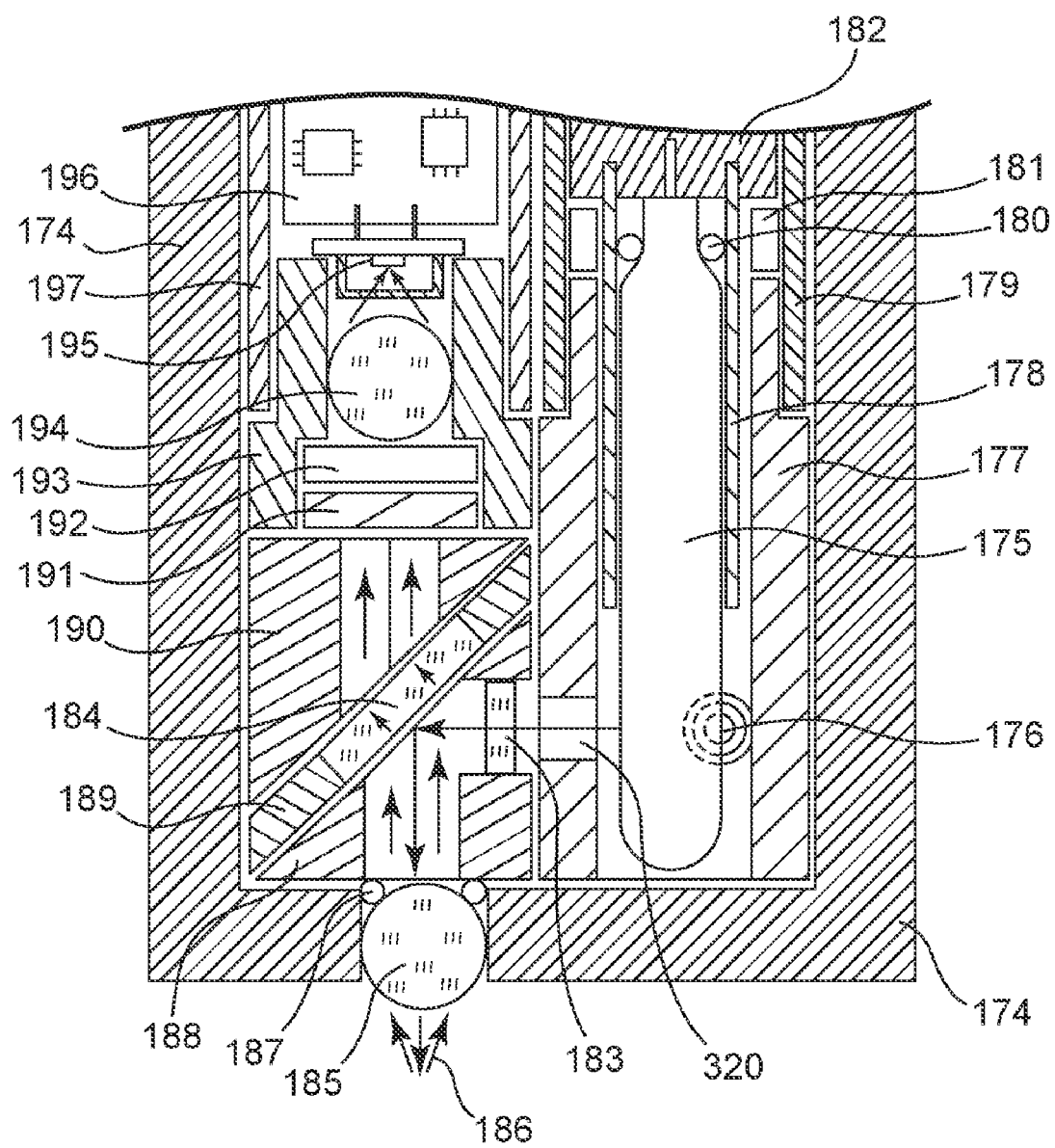
FIG. 12 shows an embodiment of the invention with a flat bottom for measuring sample solutions a high concentration of analyte and/or a high turbidity.

FIG. 12 shows an embodiment of the invention with a flat bottom for measuring sample solutions a high concentration of analyte of 500-5000 ppm and/or a high turbidity of 10-100 NTU. Instead of the 45-degree tilted bottom surface as shown in FIG. 5A, or the 90 degree geometry as shown in FIG. 8, this embodiment provides a flat bottom for a sensor head 174. The light source chamber on the right has a UV lamp 175, a reference diode 176 (set at the same height as a opening between the light source chamber and the detector chamber), an UV lamp holder 177, an UV lamp shield 178, a power supply shield 179, a lamp o-ring 180, a sealing rubber plug 181 and a power supply board 182. The detector chamber includes a short pass UV interference filter 183, a UV dichroic mirror 184, an light source/emission window-focusing mean (e.g., a sapphire ball lens) 185, a window o-ring 187, a first insert (with an excitation filter) 188, a mirror mount disk 189, a second insert 190, a glass filter of WG280 191, a glass filter of UG11 192, an optics insert 193, a photodiode ball lens 194, and a UV photodiode 195 soldered on a preamplifier board 196 shielded in a shield 197 made of a brass tube. The first insert 188 and the second insert 190 support the mirror mount disk 189 tilted at a 45-degree angle. The UV short pass filter 183 is an interference filter having a high transmission for a wavelength at 254 nm and a low transmission for longer wavelengths from 260 nm to 400 nm. The UV dichroic mirror 184 has a high reflection for wavelengths shorter than 260 nm and a high transmission for wavelengths longer than 280 nm.

The sensor head 174 uses the sapphire ball 185 as both the light source chamber window as well as the detector window to provide an analytical area 186. In this embodiment, the UV radiation emitted by the lamp 175 passes through the opening 320, the interference filter 183, to be reflected by the UV dichroic mirror 184 to the sapphire ball 185, and then arrives at the analytical area 186. The UV radiation in the analytical area 186 produces a fluorescence. The fluorescent UV signal, which travels back to the sapphire ball 185, has wavelengths longer than 280 nm and passes through the UV dichroic mirror 184, the glass filters 191, 192 and the photodiode ball lens 194, and finally reaches the UV photodiode 195. The reference diode 176 measures an intensity of UV radiation from the UV lamp 175 to provide a correction for the fluorescent signal, which is proportional to a concentration of analyte in the analytical area 186. The analytical area 186 is closer to the bottom of the sensor head 174 than the analytical area 139 to the 90 degree geometry of the sensor head 136 (FIG. 9) or the analytical area to the 45-degree tilted bottom of the sensor head 67 (FIG. 5A). This embodiment measures a fluorescent signal in very close proximity to the focusing sapphire ball lens 185 and provides a higher sensitivity for measuring fluorescence in solutions with a high turbidity or with a high analyte concentration, where the excitation radiation and the fluorescent radiation can not travel for a long distance due to high attenuation. There is another variant embodiment where, instead of one set of filters 191 and 192 and one photodiode 195, several sets of filters and several photodiodes or a linear detector array are used to measure fluorescent signals for several wavelengths.

Figure 13:
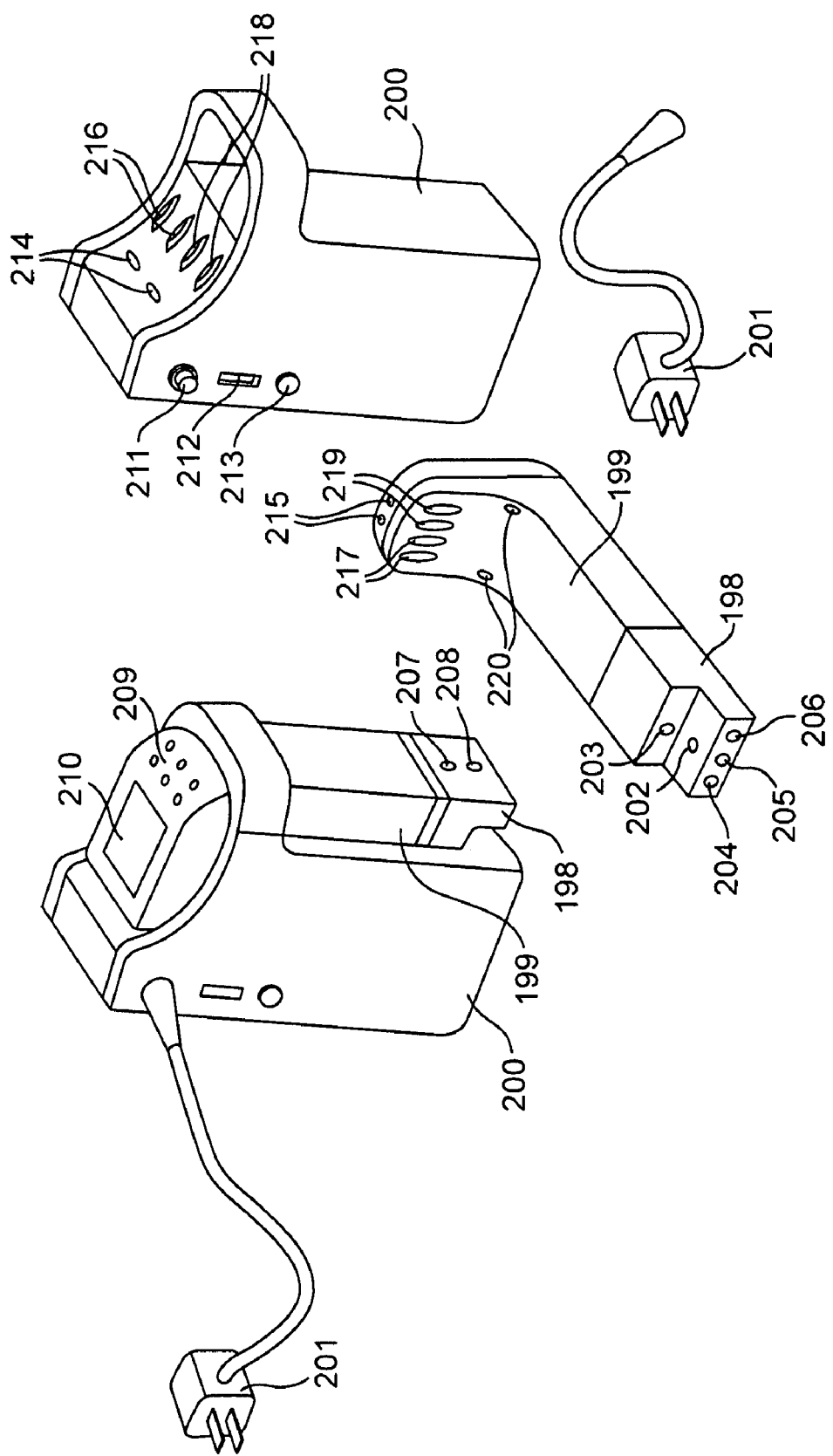
FIG. 13 shows a portable/rechargeable multi-parameter sensor with a docking station according to the invention.

FIG. 13 shows a portable/rechargeable multi parameter sensor 199 with a docking station 200 of the invention. The embodiment combines the fluorometric sensor 4 and the display unit 5 in FIG. 3 or FIG. 4 into an integrated rechargeable unit such that the sensor can be moved freely without the restraint of a power cable. The portable/rechargeable multi parameter sensor 199 is generally L-shaped to be grabbed by four fingers onto the body with a thumb up, ready to press on a keypad 209 (as with a flight simulator). The portable multi parameter sensor 199 has a sensor head 198 on a measuring end, the keypad 209 and a display 210 on a recharging end. IR (or other wireless) communication means 215, serial communication means 217 and a power input 219 are provided on the recharging end to contact corresponding elements of the wall-mounted docking station 200. Screws 220 are used to secure the inside components to the housing of the portable multi parameter sensor 199. The sensor head 198 has a light source/excitation window 202, a detector window 203 in its 90-degree geometry, a temperature sensor/detector 204, an oxidation reduction potential (ORP) sensor/detector 205, a pH sensor/detector 206 on its bottom surface, as well as a conductivity sensor/detector 207 (for measuring the conductivity of an analytical solution) and a ground pin 208 visible from its side surface. The docking station 200 has a docking loop for receiving the sensor 199 set in reverse L-shape. The docking station 200 can be stand alone or wall-mounted. The docking station 200 has a detachable transformer 201, a power connector 211 for connecting with the transformer 201, a USB connector 212, an output connector 213, IR (or other wireless) communication means 214 for wireless communication with the serial communication means 215 of the sensor 199, docking station serial communication means 216 for receiving the serial communication means 217 of the sensor 199, and a power charger output 218 for receiving the power input 219 of the sensor 199. Since the sensor 199 and the docking station 200 have limited memory and processing resources, they may connect to or wirelessly communicate with a computer or other external equipment through the USB connector 212, or the output connector 213. For example, the sensor 199 and the docking station 200 may require modified or updated operation or user data information.

Figure 14:
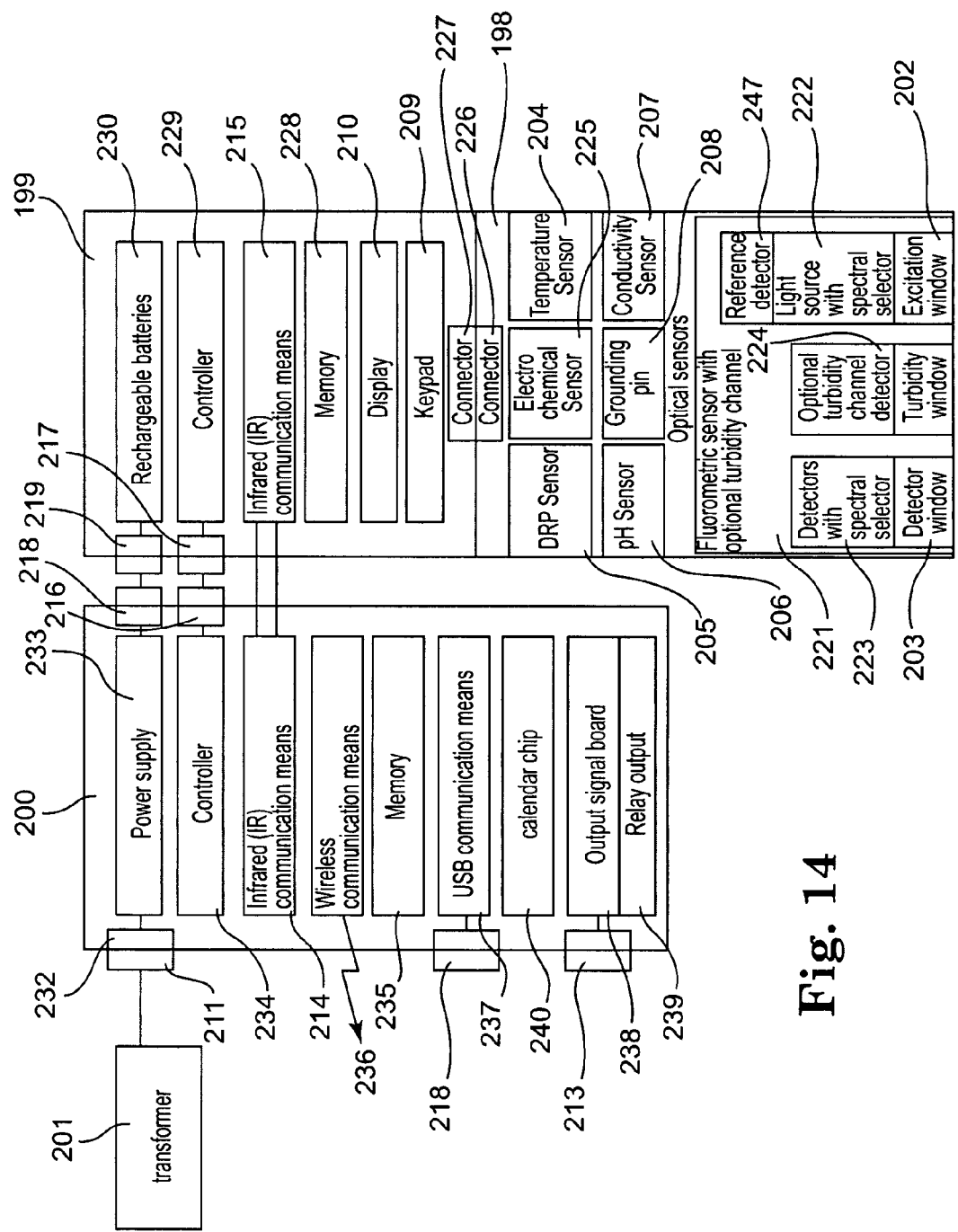
FIG. 14 shows an electrical block diagram of the embodiment of FIG. 13.

FIG. 14 shows an electrical block diagram of the embodiment of the invention of FIG. 13. The sensor head 198 has a connector 226 connected with a connector 227 of the sensor 199 thus being detachable therefrom for repair or replacement. Rechargeable batteries 230 of the sensor 199 are connected to a power supply 233 of the docking station 200 through its power input 219 connecting with the power charger output 218 of the docking station 200. The power supply 233 of the docking station 200 is then connected to the transformer 201 through its internal power supply connector 232 connecting with its externally visible power connector 211. A controller 229 of the sensor 199 is connected to a controller 234 of the docking station 200 through its serial communication means 217 contacting with the docking station serial communication means 216.

Inside the sensor 199, there are a fluorometric sensor 221 with an optional turbidity channel (e.g., the embodiments depicted in FIG. 9, FIG. 10B, FIG. 12 or the one shown in FIG. 15), a light source with spectral selector 222, a detector with spectral selector 223, a turbidity sensor 224, an optional electrochemical sensor 225 (e.g., an ISE sensor, an ion selective electrode sensor for chlorine or nitrite, for example), a memory 228, and a reference detector 247. Inside the docking station 200, there are a memory 235, wireless communication means 236, a USB communication means 237, an output signal board 238, a relay outputs and analog outputs 239, and a calendar chip 240 (for providing a real time stamp associated with a measurement result).

Figure 15:
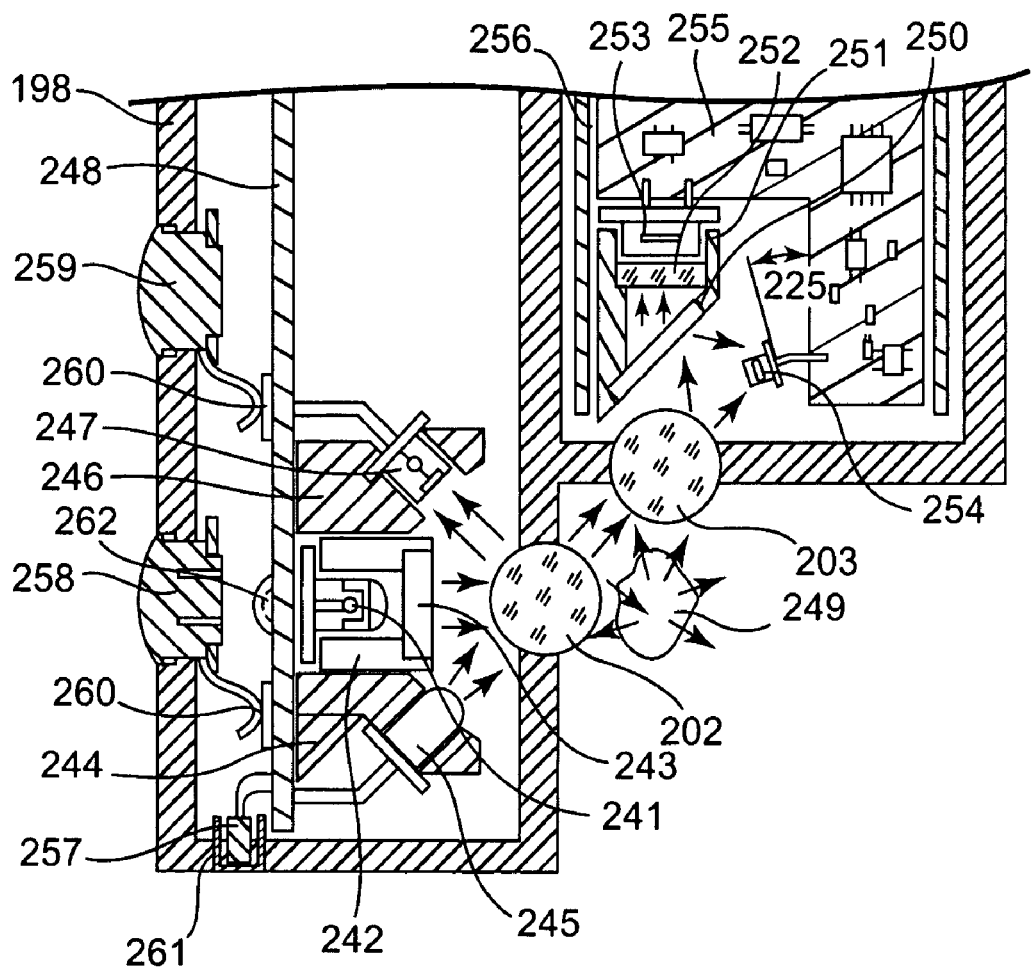
FIG. 15 shows one embodiment of the fluorescence sensor head of FIG. 13.

FIG. 15 shows one embodiment of the fluorescence sensor head 198 of FIG. 13. The sensor head 198 has a UV LED (e.g., UV LED-255 by Photon Systems, Inc., Covina, Calif.), a light source/turbidity channel, a detector channel, a reference channel and a channel for monitoring an optical transmission of the ball lenses. The fluorescence sensor head 198 has two ball lens 202, 203 functioning as the excitation window-focusing means 137 and the detector window-focusing means 138 in FIG. 9, but moves the detector chamber back to right and adds a GaN photodiode 254 being tilted at 22.5-degree to function as a turbidity direct light detector and a detector for optics transmittance validation. In the detector chamber on the right side of FIG. 15, a 45-degree dichroic filter 250, a holder 251 for the 45-degree dichroic filter 250, a glass filter 252 of model WG280, a UV photodiode 253, a preamplifier board 255, and a shield 256 are provided similarly to the corresponding components in the left channel in FIG. 9. In the light source/turbidity channel on the left side of FIG. 15, a first UV LED (255 nm) 241, a second UV LED (350 nm) 245, and a GaN photodiode 247 are soldered to a LED board 248. The first UV LED (255 nm) 241 is supported by a short pass UV filter holder 242, and covered by a short pass UV filter 243 to function as the fluorescence light source as the UV lamps in the above-discussed embodiments. The second UV LED (350 nm) 245 is supported by a second UV LED (350 nm) holder 244 to function as a light source for the optics transmittance validation channel. The GaN photodiode 247 is supported by a GaN photodiode holder 246 to function as a reference detector for monitoring the UV intensity of the first UV LED (255 nm) 241 and the second UV LED (350 nm) 245. The 45-degree dichroic filter 250 has a high reflection for wavelengths shorter than 260 nm and a high transmission for wavelengths longer than 280 nm.

The fluorescence measuring operation of this embodiment is similar to the embodiment depicted in FIG. 9. The first UV LED 241 emits a UV radiation of 255 nm which passes the short pass UV filter 243 and the ball lens 202 to an analytical area 249, where it produces from analyte a fluorescent signal with wavelengths shifted relative to the excitation wavelength and proportional to an analyte concentration. It also produces a scattered signal, which has an identical wavelength as the excitation wavelength and proportional to a turbidity of the sample. Thereafter the fluorescent signal from the analytical area 249 passes the ball lens 203, the 45-degree dichroic filter 250, and reaches the UV photodiode 253. The turbidity signal from analytical area 249 passes the ball lens 203 reflects from, the 45-degree dichroic filter 250, and reaches the UV photodiode 254. This embodiment provides one additional operation of measuring the cleanness of the balls lenses 202, 203. A light of 350 nm passes the ball lenses 202 and 203 to the GaN photodiode 254 from the UV LED 245 to monitor an optical transmission of the ball lenses so as to determine if the surfaces of the ball lenses were contaminated. The reference photodiode 247 measures a signal emitted by the UV LED (350 nm) 245 and then reflected by the ball lens 202 for monitoring the UV intensity of the UV LED (350 nm) 245. Similar to the embodiment depicted in FIG. 5B, the fluorescence sensor head 198 also has a temperature sensor 257 and a temperature sensor insert 261. Similar to the embodiment depicted in FIG. 13, the fluorescence sensor head 198 also provides a ground pin 258 and a conductivity sensor 259 which are connected to the LED board 248 through spring contacts 260. An UV LED emits focused light in a desired direction, while the UV lamp emits in all directions and produces unnecessary heat. By replacing the UV lamp in FIG. 9 with the UV LED (255 nm) 241 in FIG. 15, this embodiment reduces power consumption and heat emission.

Although the embodiments discussed above are described with respect to example wavelength ranges, it shall be understood that the invention is not limited to particular wavelengths or wavelength ranges, and that the embodiments described herein are for exemplary only. It shall also be understood that although particular components may be shown and described, the invention is similarly not limited to any particular components or physical configurations of those components.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The terms "controller," "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM).

In general, fluorometric sensors are more sensitive than absorbance sensors. In other words, less fluorescent material is needed to obtain a measurement using a fluorometric sensor than if the same material was measured using an absorbance sensor. This allows the fluorescent sensor to be used with low concentration products where absorbance sensors would not be effective.

Additionally, the nature of fluorescent sensor allows flexibility with regard to the placement of the sensor. Specifically, an absorbance sensor requires a linear path where light is shined through a cell. The fluorescent sensor of the present invention does not require a linear path and can therefore be used like a port where the port can simply be placed in a liquid or gaseous medium and provide a measurement. This allows flexibility if the fluorescent sensor is placed for example in a warewashing machine, sink, mop bucket, laundry machine and the like.

A fluorescent sensor also has increased specificity due to selection of specific absorption and emission wavelengths compared to an absorbance sensor which only selects the absorbance wavelength. This allows for direct measurement of a fluorescent material (versus inferring concentration through the measurement of a tracer). Additionally, the fluorometric sensors of the present invention may be used to determine the presence of compounds or substances that are not supposed to be in a product or composition, for example, contaminations such as soils, hard water, bacteria, and the like.

Determining a product concentration is useful in many applications, especially determining the product concentration of a cleaning or antimicrobial product. Cleaning and antimicrobial products are used in many different applications including laundry, automatic ware-washing, manual ware-washing, $3^{rd}$ sink applications, power sink applications, vehicle care, clean-in-place operations, healthcare applications, hard surface applications and the like. The fluorometric sensor of the present invention can be used to determine the concentration of the cleaning or antimicrobial product in any or all of these applications.

In laundry applications, detergent compositions, fabric softeners, fabric brighteners, antimicrobial agents and bleaches, are used to clean and reduce the microorganism population on textiles, such as bedding, towels, clothes and uniforms. The laundry application may include home laundry applications, laundromats, on-premise laundry facilities in hotels and motels and commercial laundry facilities. The products can be dispensed in a number of ways. Typically, product is dispensed similar to ware-washing dispensing and then the product is flushed into the machine. The products can take on a number of forms including concentrates and ready-to-use compositions, liquid, gel, emulsion, foam, tablet, solid, powder, water soluble film with product inside, or a woven or non-woven substrate with product adhered onto it. Additional examples of laundry applications are described in U.S. Pat. Nos. 5,861,371, 6,253,808, 6,444,023, 6,627,592, and application Ser. Nos. 10/435,342 and 10/826,825, the complete disclosures of which are incorporated by reference herein in their entirety. The sensor of the present invention measures fluorescence in a liquid solution or measures fluorescence by looking through a gas (i.e., air) at a surface. The sensor can be connected to the device or can be a fiber optic. When used in laundry applications specifically, some non-limiting examples for deploying the sensor of the present invention include measuring the liquid coming out of a dispenser that is flushed into the machine, measuring the liquid being pumped out of the machine after the laundry cycle is complete, or measuring liquid in the holding tank.

In ware-washing applications, detergent compositions, rinse aids, antimicrobial agents and the like are dispensed in various cycles into a ware-washing machine to wash dishes, glassware, utensils, and pots and pans. The products can be dispensed into a number of types of machines including traditional consumer automatic dishwashing machines and institutional ware-washing machines (such as door or hood machines, conveyor machines, under-counter machines, glass-washers, flight machines, pot and pan machines, and utensil washers). The product can be dispensed using a variety of dispensing mechanisms including pumps (e.g., peristaltic, bellows, and the like), syringe/plunger injection, gravity feed, siphon feed, aspirators, unit dose (e.g., a water soluble packet such as polyvinyl alcohol, a foil pouch, a "pill" or "gum ball" dispenser that drops a tablet into the machine), evacuation from a pressurized chamber, diffusion through a membrane or permeable surface, and the like. In manual ware-washing applications, product is added to water, either manually or via a dispenser, and then dishes, glassware, utensils, pots and pans are washed manually. The product may be in the form of a concentrate or ready-to-use composition, and may be a liquid, gel, emulsion, foam, a tablet or other solid, a powder, a water-soluble film with product inside, or a woven or non-woven substrate with product adhered or impregnated onto it. A $3^{rd}$ sink refers to an additional sink in a restaurant that includes a sanitizer. Once a dish, glass, utensil, pot or pan is washed manually, it is placed in a $3^{rd}$ sink to be sanitized. A power sink refers to a sink that has a pump or other means of providing agitation to the water. It is a cross between an automatic ware-washing machine and manual ware-washing and can be found in quick service restaurants. Products used in power sink applications are similar to those used in manual ware-washing applications although they may be formulated slightly different to account for the unique characteristics of a power sink application such as foam generation. The products used in power sink applications can be dispensed in a manner similar to manual ware-washing applications. Additional examples of ware-washing applications are described in U.S. Pat. Nos. 5,358,653, 5,880,089, 6,150,324, 6,177,392, 6,258, 765, 6,294,515, 6,436,893, 6,503,879, 6,583,094 6,653,266 and RE32,818, the complete disclosures of which are incorporated by reference herein in their entirety. Some non-limiting examples for deploying the sensor in ware-washing applications include measuring in the solution coming out of the dispenser and/or going into the ware-washing machine, in the machine itself, in the sump, in the solution being pumped out of the ware-washing machine, and in a sink such as a power sink, a $3^{rd}$ sink, or a manual washing sink.

In vehicle care applications, products such as detergents, sheeting compositions, waxes, glass cleaners, wheel cleaners, rust inhibitors, Rain-X, and clear coat-protectants are applied to vehicles (e.g., consumer vehicles, commercial vehicles, rental vehicles, fleet vehicles, etc.). The products may be applied manually or as part of a car wash including automatic car washes, tunnel car washes and the like. These products are dispensed manually into a spray bottle, or bucket, or automatically such as through a dispenser such as that described above with respect to ware-washing. The product may be applied to a vehicle manually by spraying or wiping, or may be applied automatically by spraying. Additional examples of vehicle care applications are described in U.S. Pat. Nos. 5,871,590 6,339,054, 6,645,924, 6,726,779, 6,821,351 and 6,864,220, the complete disclosures of which are incorporated by reference herein in their entirety. Some non-limiting examples for deploying the sensor in vehicle care applications include mounted on the wall or spray arm measuring the surface of the car through the air, measuring in bucket or spray bottle, measuring in the automatic spray washing arm of an automatic car wash, and measuring in a holding tank.

In clean-in-place (CIP) operations, detergent compositions, antimicrobials and the like are pumped through a circuit. The combination of the chemistry and mechanical action of the compositions cleans the inside of the circuit without requiring the entire circuit to be disassembled and cleaned manually which is very time consuming and labor intensive. CIP cleaning is used, for example, to clean food and beverage, pharmaceutical, and cosmetic processing equipment. A more detailed discussion of CIP operations is found in U.S. Pat. Nos. 5,858,117, 6,197,739, 6,953,507 and 6,991,685, the complete disclosures of which are incorporated by reference herein in their entirety. Some non-limiting examples for deploying the sensor in clean-in-place applications include measuring in the CIP circuit such as in a pipe or tank or vessel, in the line after the product is dispensed but prior to putting the product in the CIP circuit, and in the line as product is being pumped out of the circuit.

In healthcare settings, detergents, antimicrobials, and the like are used to meet the stringent cleaning and microorganism reduction demands of healthcare facilities, such as hospitals, nursing homes and long term care facilities, dental offices, clinics, and surgical suites. Detergents and antimicrobials are used to clean and disinfect textiles, such as bedding, towels, clothes, uniforms, and patient garments, hard surfaces (such as floors, walls, countertops, beds, and bathroom, operating room and patient room fixtures), and medical instruments (such as surgical instruments, dental instruments, examination instruments, and endoscopes). A more detailed description of healthcare applications is found in U.S. Pat. Nos. 4,994,200 5,223,166, 5,234,832, 5,403,505 6,627,657, 6,908,891 and 6,998,369, the complete disclosures of which are incorporated by reference herein in their entirety. Some non-limiting examples for deploying the sensor in healthcare applications include those already described with respect to laundry facilities and ware-washing applications. Hard surface applications are described in greater detail as follows.

In hard-surface applications, glass-cleaners, floor cleaners, antimicrobials, degreasers, multipurpose cleaners and the like are used to clean and reduce microorganisms on hard-surfaces including but not limited to floors, walls, countertops, room fixtures, drains, etc. Hard surface cleaners and antimicrobials can be applied to the hard-surfaces by spraying, misting, wiping, rolling, fogging and mopping. The cleaner or antimicrobial can be a liquid, gel, emulsion, concentrate, ready-to-use solution, or can be adhered or impregnated onto a woven or non-woven textile. The cleaner or antimicrobial can be a solid, powder or prill that is added to a liquid to form a use solution. A more detailed description of hard-surface applications is found in U.S. Pat. Nos. 5,019,346, 5,200,189, 5,312,624, 5,314,687, 5,234,719, 5,437,868, 5,489,434, 5,718,910, 6,197,321, 6,268,324, 6,472,358, 6,530,383 and 6,630,434, the complete disclosures of which are incorporated by reference herein in their entirety. Some non-limiting examples for deploying the sensor c in hard-surface applications include measuring in a spray bottle, in a bucket, and on a handheld sensor or wand.

Additionally, the sensor can be used to determine the concentration of a pesticide in pest control operations. A more detailed description of pest applications is found in U.S. Pat. Nos. 5,464,613, 5,820,855, 5,914,105, 6,153,181, 6,564,502, 6,725,597, 6,877,270 and 6,937,156, the complete disclosures of which are incorporated by reference herein in their entirety. For example, for a pesticide sprayed in a room, such as around baseboards or on fixtures, a sensor mounted on a handheld device or wand can be used to determine the concentration of the pesticide after application or after a period of time has elapsed.

The sensor can also be used to determine the concentration or presence of a floor care product, both before and after it is applied to a floor. This can be used, for example, to determine if the product on the floor needs to be removed, if a new coating needs to be applied, and the status of the coating prior to application onto the floor. A more detailed description of floor care application is found in U.S. Pat. Nos. 6,695,516, 6,799,916, 6,800,353, 6,822,030, 6,822,063, 6,828,296 and 6,955,490, the complete disclosures of which are incorporated by reference herein in their entirety. Some non-limiting examples for deploying the sensor in floor care applications include incorporated onto or into a handheld sensor or wand that can measure the fluorescence of a floor care composition on a floor, and measuring the floor care composition packaging before it is applied to a floor.

The sensor can be used to determine the concentration of an additive in a pool or spa. A more detailed description of pool and spa applications is found in U.S. Pat. Nos. 6,398,961 and 6,506,737, the complete disclosures of which are incorporated by reference herein in their entirety. Some non-limiting examples for deploying the sensor in pool and spa applications include measuring inside the pool or spa.

The sensor can be used to determine the concentration of products used to treat water such as drinking water, heating water, cooling water and wastewater. A more detailed description of water care applications is found in U.S. Pat. Nos. 6,398,961, 6,506,737 and 6,555,012, the complete disclosures of which are incorporated by reference herein in their entirety. Some non-limiting examples for deploying the sensor in water care applications include measuring in the water circuit or being incorporated into a handheld sensor or wand that can be placed into the water.

The sensor can be used to determine the concentration of an antimicrobial for application on meat carcasses. A more detailed description of carcass treatment is found in U.S. Pat. Nos. 5,122,538, 5,200,189, 5,314,687, 5,437,868, 5,489,434, 5,718,910, 6,010,729, 6,103,286, 6,113,963, 6,183,807 6,514,556 and 6,545,047, the complete disclosures of which are incorporated by reference herein in their entirety. Some non-limiting examples for deploying the sensor, in carcass applications include measuring in a dip tank, in a chiller, incorporated into a handheld device or wand that can be placed in a solution such as a dip tank, in a spray cabinet prior to application onto a carcass, and measuring in the spray cabinet looking at the carcass after product has been applied.

The sensor can be used to determine the concentration of an antimicrobial used in aseptic packaging operations and bottle washing operations. In aseptic packaging and bottle washing operations, containers are inverted and sprayed with a solution which is then drained out. The product is collected and re-circulated for application onto new bottles or packages. A more detailed description of aseptic packaging and bottle washing operations is found in U.S. Pat. Nos. 6,326,032, 6,530,386, 6,593,283 and 6,998,369, the complete disclosures of which are incorporated by reference herein in their entirety. Some non-limiting examples for deploying the sensor in aseptic packaging and bottle washing operations includes measuring in the recirculation tank, looking at the bottles, and measuring in the line prior to application onto the bottles or packages.

The sensor can be used to determine the concentration of a lubricant in food or beverage conveying operations. In food or beverage plants, lubricants are needed to lubricate the interface between the package and the conveyor. A more detailed description of lubricant technology is found in U.S. Pat. Nos. 5,391,308, 5,932,526, 6,372,698, 6,485,794, 6,495,494 and 6,667,283, the complete disclosures of which are incorporated by reference herein in their entirety. Some non-limiting examples for deploying the sensor include measuring above the conveyor after the lubricant is applied but before the packages are placed on the conveyor, or measuring after the packages are moved off the conveyor but before lubricant is applied.

The sensor of the present invention can be used to sense a wide variety of products used in the applications described above because many of the compounds that make up the products have fluorescent characteristics.

Generally, a compound or molecule that has a benzene component

multiple conjugated bonds, electron donating groups such as —OH, —NH$_2$, and —OCH$_3$, and polycyclic compounds exhibit fluorescent characteristics. Many compounds used in the above-described applications include chemical structures like these, such as surfactants, lubricants, antimicrobial agents, solvents, hydrotropes, antiredeposition agents, dyes, corrosion inhibitors and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like.

Some non-limiting examples of fluorescent surfactants include aromatic phosphate esters, nonyl and octylphenol alkoxylates, alkylbenzene sulfonate, sodium xylene sulfonate, sodium toluene sulfonate, sodium cumene sulfonate, ethoxylated alkyl phenol sulfonates, alkyl naphthalene sulfonates, naphthalene sulfonate formaldehyde condensates, benzothiazole, benzotriazole, aromatic hydrocarbons, benzoic acid, sodium benzoate, sodium salicylate para-chloro-meta-xylenol, orthophenyl phenol, fragrances, chlorobisphenols.

Some non-limiting examples of fluorescent antimicrobial agents include alklyldimethylbenzyl ammonium chloride, glutaraldehyde, chlorophenols, amylphenol, and alkyl dimethyl benzyl ammonium saccharinate.

Some non-limiting examples of fluorescent solvents include aromatic hydrocarbons.

Some non-limiting examples of fluorescent hydrotropes include linear alkyl benzene or naphthaline sulfonates such as sodium zylene sulfonate.

Some non-limiting examples of fluorescent antiredeposition agents include acid anhydride copolymers such as styrene maleic anhydride copolymers.

Some non-limiting examples of fluorescent dyes include 2-naphthalenesulfonic acid, Acid Yellow 7,1,3,6,8-pyrenetetrasulfonic acid sodium salt, and fluorescein.

Some non-limiting examples of fluorescent corrosion inhibitors include benzotriazole, tolyltriazole, 5-methyl benzotriazole (5-MBz), and 1-hydroxy benzotriazole.

Some non-limiting examples of fluorescent bleaching additives include phthalimido-peroxy hexanoic acid.

It is understood that compounds known to a person skilled in the art fall into the categories described above (e.g., surfactants, solvents, antimicrobial agents, and the like) and that a person skilled in the art will be able to select those compounds that exhibit fluorescent characteristics to formulate cleaning and antimicrobial products accordingly.

The product can take on a variety of physical forms. For example, the product can be a concentrate or a ready-to-use composition. The concentrate refers to the composition that is diluted to form the ready-to-use composition. The ready-to-use composition refers to the composition that is applied to a surface. The concentrate and ready-to-use composition can be a liquid, gel, emulsion, solid, tablet, powder, prill, gas and the like. The product can be designed for institutional or industrial use or the product can be unit dose (e.g., a spray bottle or a unit dose container such as a foil pouch or water soluble pouch).

Additionally, tracers can be incorporated into products that may or may not already include naturally fluorescing compounds. Some non-limiting examples of tracers include 2-naphthalenesulfonic acid, Acid Yellow 7,1,3,6,8-pyrenetetrasulfonic acid sodium salt, and fluorescein.

As discussed, the sensor of the present invention can be placed in several different places in order to measure fluorescence. For example, the sensor can be placed inside a warewashing machine or laundry machine, inside a sink, in a mop bucket, in a pipe, in a tank, mounted on another sensor or handheld device that can be placed next to a floor to read the fluorescence of a floor care composition, next to or near a spray nozzle or in the path of the spray pattern (e.g., a lubricant spray nozzle, a spray nozzle in a cabinet for treating carcasses), in a healthcare instrument reprocessor, inside a cooling or heating tower, in a pool or spa, in or near a product dispenser, and the like.

As discussed, the sensor of the present invention can be used to determine the concentration of a product. Accordingly, the sensor can be part of a feedback loop where a preferred concentration is determined. If the sensor determines that the concentration is lower or higher than a threshold concentration, it can signal the dispenser to adjust appropriately by either dispensing more or less product. A feedback loop will ensure that enough cleaner, antimicrobial or other composition is present to achieve the desired effect (cleanliness, reduction in microorganisms, lubrication, etc.).

Additionally, the sensor of the present invention can function as part of an out-of-product alarm. When a product runs out, the fluorescence (which reflects the concentration of the product) will drop below a pre-determined threshold level. At this point, the sensor can generate a signal alerting an operator that the dispenser is out of product. The signal can be a visual or audio signal, or a vibrating signal. The signal can be an electronic signal that tells the machine or dispenser to stop operating until an additional amount of the product is placed into a dispenser. The signal can be wired, for example, to a light, an audible alarm or a dispenser. Alternatively, the signal can be wireless and function with a dispenser or dispensers on the other side of a room, or with a web-based system. In a web-based system, a supplier, a customer, a service providing company and/or a service technician can be alerted that a dispenser is out of product. This way, the supplier, the customer, the service providing company and/or the service technician can monitor multiple locations from one computer and dispatch someone to add additional product.

Many principles, embodiments and modes of operation of the present invention have been described. However, the invention, which is intended to be protected, is not limited to the particular embodiments disclosed. The embodiments described herein are illustrative rather than restrictive. Variations and changes may be made by others, and equivalents employed, without departing from the spirit of the present invention. These and other embodiments are within the scope of the following claims.

The invention claimed is:

1. A sensor, comprising:
a sensor head having a 90 degree cutout in a lateral surface, the 90 degree cutout defining a first planar surface intersecting at 90 degrees to a second planar surface, the sensor head comprising:
a light source chamber including an ultraviolet (UV) light source that emits a first UV wavelength;
a light source window positioned in the first planar surface that transmits the first UV wavelength into an analytical area containing a sample having an unknown concentration of a chemical that exhibits fluorescent characteristics;
a detector window positioned in the second planar surface; and
a detector chamber including a UV detector that detects fluorescence emissions of the sample at a second UV wavelength transmitted through the detector window; and
a controller that calculates the concentration of the chemical in the sample based on the detected fluorescence emission.

2. The sensor of claim 1 wherein the controller calculates the concentration of the chemical in the sample based on a calculated difference in the detected fluorescence emission of the sample and a detected fluorescence emission of a zero solution having zero concentration of the chemical.

3. The sensor of claim 1 wherein the controller calculates the concentration of the chemical in the sample based on the detected fluorescence emission of the sample and a calibration constant determined for known concentrations of the chemical.

4. The sensor of claim 1 further comprising a second UV detector that detects reference fluorescence emissions of the sample at the first UV wavelength.

5. The sensor of claim 1 wherein the second UV wavelength is in a range of 280 nanometers±15 nanometers.

6. The sensor of claim 1 wherein the first UV wavelength is approximately 254 nanometers.

7. The sensor of claim 1 wherein the chemical is an antimicrobial agent.

8. The sensor of claim 1 wherein the sample is a solution containing the chemical, wherein the solution is a cleaning or antimicrobial solution, and wherein the chemical is selected from the group consisting of antimicrobial agents, surfactants, solvents, hydrotropes, antiredeposition agents, dyes, corrosion inhibitors, bleaching agents and mixtures thereof.

9. The sensor of claim 1 wherein the ultraviolet light source is one of a gas discharge lamp, a mercury lamp, a deuterium lamp, a metal vapor lamp, a light emission diode or a plurality of light emission diodes.

10. The sensor of claim 1 wherein the ultraviolet light source is one of a mercury low pressure lamp with main line at about 255 nm or a Krypton gas discharge lamp.

11. The sensor of claim 1 further comprising a second UV detector that monitors an intensity of the UV light source.

12. The sensor of claim 1 wherein the light source window includes one of a first prismatic window or a first ball lens and the detector window includes one of a second prismatic window or a second ball lens.

13. The sensor of claim 1 further comprising at least one of a reference detector, a turbidity detector, a temperature detector, an oxidation reduction potential detector, a pH detector, a conductivity detector and an electro chemical detector.

14. The sensor of claim 1 wherein the chemical is a multiquat sanitizer.

15. The sensor of claim 1, further comprising:
a plurality of light source windows positioned in the first planar surface; and
a plurality of detector windows positioned in the second planar surface, each of the plurality of detector windows corresponding to a different one of the plurality of light source windows.

16. The sensor of claim 15, further comprising:
a plurality of optical filters, each positioned in the light source chamber between the UV light source and a different one of the plurality of light source windows.

17. The sensor of claim 15, wherein the detector chamber further includes:
a plurality of detectors each corresponding to a different one of the detector windows; and
a plurality of detector filters, each positioned in the detector chamber between a different one of the plurality of detector windows and the corresponding detector.

18. The sensor of claim 1 wherein the controller calculates the concentration of the chemical in the sample using the equation:

$$C = K_x (I^S_{280}/I^S_{254} - I^0_{280}/I^0_{254})$$

wherein C is a concentration of the chemical in the sample, $K_x$ is a calibration coefficient, $I^S_{280}$ is an output signal from the first detector for the sample, $I^S_{254}$ is an output signal from the second detector for the sample, $I^0_{280}$ is an output signal from the first detector for a zero solution (i.e., a solution with zero concentration of the chemical), $I^0_{254}$ is an output signal from the second detector for the zero solution, and $$K_x = C_{CCALIBR}/(I^{CALIBR}_{280}/I^{CALIBR}_{254} - I^0_{280}/I^0_{254})$$

where $C_{CALIBR}$ is a concentration of the chemical in a calibration solution, $I^{CALIBR}_{280}$ is an output signal from the first detector for the calibration solution and $I^{CALIBR}_{254}$ is an output signal from the second detector for the calibration solution.

19. The sensor of claim 1 wherein the controller further calculates a turbidity of the sample.

20. The sensor of claim 1 wherein the sensor head is substantially cylindrical and having the 90 degree cutout parallel to an axis of the cylinder on a lateral surface of the sensor head.

* * * * *